United States Patent [19]

Tsujihara et al.

[11] 4,182,757
[45] Jan. 8, 1980

[54] NOVEL NITROSOUREA COMPOUNDS AND PROCESS FOR PREPARING THE SAME

[75] Inventors: Kenji Tsujihara, Urawa; Masakatsu Ozeki, Wako; Yoshihisa Arai, Urawa, all of Japan

[73] Assignee: Tanabe Seiyaku Co., Ltd., Osaka, Japan

[21] Appl. No.: 922,811

[22] Filed: Jul. 10, 1978

[30] Foreign Application Priority Data

Jul. 29, 1977 [JP] Japan .................................. 52/91674
Sep. 22, 1977 [JP] Japan .................................. 52/114259
Feb. 2, 1978 [JP] Japan .................................. 53/11225
May 16, 1978 [JP] Japan .................................. 53/58560
May 26, 1978 [JP] Japan .................................. 53/63459

[51] Int. Cl.$^2$ .................... A61K 31/70; C07H 15/02
[52] U.S. Cl. ..................... 424/180; 536/22; 536/53; 536/4
[58] Field of Search ................ 536/4, 18, 22, 53; 424/180

[56] References Cited

U.S. PATENT DOCUMENTS

| | | | |
|---|---|---|---|
| 3,577,406 | 5/1971 | Hessler | 536/53 |
| 3,767,640 | 10/1973 | Suami et al. | 536/4 |
| 3,940,383 | 2/1976 | Fujiwara et al. | 536/18 |
| 4,057,684 | 11/1977 | Kimura et al. | 536/18 |
| 4,086,415 | 4/1978 | Suami et al. | 536/53 |

*Primary Examiner*—Johnnie R. Brown
*Assistant Examiner*—Blondel Hazel
*Attorney, Agent, or Firm*—Bierman & Bierman

[57] ABSTRACT

A nitrosourea compound of the formula:

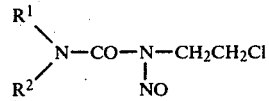

wherein $R^1$ is alkyl of one to six carbon atoms, hydroxyalkyl of one to six carbon atoms, alkenyl of three to five carbon atoms or alkynyl of three to five carbon atoms, $R^2$ is aldopentofuranosyl, aldo-pentopyranosyl, aldo-hexopyranosyl, O-aldo-hexopyranosyl-(1→4)-aldo-hexopyranosyl or a group of the formula: —CH$_2$(CHOH)$_n$CH$_2$OH, and wherein n is zero or an integer of one to four. A method of preparation is disclosed whereby said nitrosourea compound is prepared by the nitrosation of a compound of the formula:

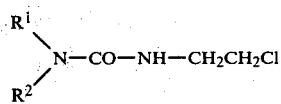

wherein $R^1$ and $R^2$ are the same as above. Said nitrosourea compound is useful as an anti-tumor or anti-leukemic agent.

47 Claims, No Drawings

NOVEL NITROSOUREA COMPOUNDS AND PROCESS FOR PREPARING THE SAME

This invention relates to a novel nitrosourea compound and a process for preparing the same. More particularly, it relates to a compound of the formula:

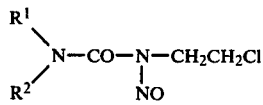

wherein $R^1$ is alkyl of one to six carbon atoms, hydroxyalkyl of one to six carbon atoms, alkenyl of three to five carbon atoms or alkynyl of three to five carbon atoms, $R^2$ is aldo-pentofuranosyl, aldo-pentopyranosyl, aldo-hexopyranosyl, O-aldo-hexopyranosyl-(1→4)-aldo-hexopyranosyl or a group of the formula: —CH$_2$(CHOH)$_n$CH$_2$OH, and wherein n is zero or an integer of one to four.

It is known that (N'-chloroethyl-N'-nitrosocarbamoyl)amino derivatives of monosaccharides are prepared by nitrosation of (N'-chloroethylcarbamoyl)amino-monosacchardies with an alkali metal nitrite such as sodium nitrite (Japanese Patent Application Nos. 31131/1975, 90266/1974 and 124319/1974 which were laid open to the public under Nos. 108043/1976, 26876/1976 and 52128/1976, respectively). These patents also disclose that 1-(2-chloroethyl)-1-nitroso-3-D-mannopyranosylurea and 1-(2-chloroethyl)-1-nitroso-3-D-glucopyranosylurea (the latter compound being hereinafter referred to as "GANU") increase the life span of mice implanted intraperitoneally with the tumor cells of lymphoid leukemia L-1210. Further, it is known that (N'-chloroethyl-N'-nitrosocarbamoyl)amino derivatives of disaccharides such as 1-(2-chloroethyl)-1-nitroso-3-D-lactosylurea and 1-(2-chloroethyl)-1-nitroso-3-D-maltosylurea are prepared from the corresponding (N'-chloroethylcarbamoyl)amino-disaccharides in the same manner as above and show anti-tumor activity against leukemic cells (Japanese Patent Application No. 64073/1975 which was laid open to the public under No. 141815/1976).

We have now found that the nitrosourea compound [I] of the present invention shows potent anti-tumor or anti-leukemic activity with low toxicity and is useful to inhibit the growth of malignant tumor cells in warm-blooded animals. For example, when the anti-tumor effect on leukemia is estimated by administering each drug intraperitoneally to tumor cell-inoculated mice (i.e., mice implanted with tumor cells of Leukemia L-1210) for five consecutive days, 1-(2-chloroethyl)-1-nitroso-3-isobutyl-3-D-galactopyranosylurea at a daily dose of 1.0 mg/kg or 1-(2-chloroethyl)-1-nitroso-3-isobutyl-3-[O-α-D-glucopyranosyl-(1→4)-D-glucopyranosyl]urea at a daily dose of 0.9 mg/kg provides for an increase of about 30% in the average life span of said mice. The preventive effect of 1-(2-chloroethyl)-1-nitroso-3-n-butyl-3-D-glucopyranosylurea, 1-(2-chloroethyl)-1-nitroso-3-isobutyl-3-D-galactopyranosylurea and 1-(2-chloroethyl)-1-nitroso-3-isobutyl-3-[O-α-D-glucopyranosyl-(1→4)-D-glucopyranosyl]urea on Ehrlich's ascites tumor is also about 8 to 16 times stronger than that of 1-(2-chloroethyl)-1-nitroso-3-cyclohexylurea (CCNU: $R^1$=H, $R^2$=cyclohexyl) disclosed in T. P. Johnson et al's J. Med. Chem. 9, 892 (1966).

Moreover, the nitrosourea compound [I] of the invention is low in toxicity and is very safe for use as an anti-tumor agent. For example, when the therapeutic index is estimated by the ratio of the optimal dose (the daily dose at which the maximum increase in the life span of tumor cell-inoculated mice occurs) to ILS$_{30}$ (the minimum daily dose which shows 30% increase in the life span of said mice) in case of leukemia L-1210, said therapeutic index of 1-(2-chloroethyl)-1-nitroso-3-isobutyl-3-isobutyl-3-[O-α-D-glucopyranosyl(1→4)-D-glucopyranosyl]urea may be more than 10 times greater than that of CCNU and GANU.

The compound [I] may also be characterized by a high therapeutic index estimated in terms of the ratio of Max. D (the maximum dose which shows 100% inhibition for the growth of Ehrlich's ascites tumor in mice without causing the death of said mice) to Min. D (the minimum dose which shows 100% inhibition for the growth of said ascites tumor). For example, said therapeutic indexes (Max.D/Min.D) of 1-(2-chloroethyl)-1-nitroso-3-n-butyl-3-D-galactopyranosylurea, 1-(2-chloroethyl)-1-nitroso-3-isobutyl-3-[O-α-D-glucopyranosyl-(1→4)-D-glucopyranosyl]urea and 1-(2-chloroethyl)-1-nitroso-3-(2-propenyl)-3-L-arabinopyranosylurea are more than 3 times greater than those of GANU and CCNU. The compound [I] of the invention may further show low bone marrow toxicity.

In the above-mentioned formula [I], representative examples of the group $R^1$ include straight or branched alkyl such as methyl, ethyl, n-propyl, isopropyl, n-butyl, isobutyl, sec.-butyl, tert.-butyl, n-pentyl, isopentyl, neopentyl, 1-methylbutyl, 1-ethylpropyl, tert.-pentyl, n-hexyl, 2-methylpentyl, isohexyl and 3,3-dimethylbutyl; straight or branched alkenyl such as 2-n-propenyl, 2-methyl-2-n-propenyl, 2-n-butenyl and 3-n-butenyl; alkynyl such as 2-propynyl, 2-butynyl, 3-n-butynyl and 2-methyl-3-butynyl; and hydroxyalkyl such as 2-hydroxyethyl and 3-hydroxy-n-propyl.

On the other hand, representative examples of the group $R^2$ include aldo-pentofuranosyl such as D-ribofuranosyl and D-deoxyribofuranosyl; aldo-pentopyranosyl such as L-arabinopyranosyl and D-xylopyranosyl; aldo-hexopyranosyl such as D-glucopyranosyl, D-galactopyranosyl, D-mannopyranosyl, L-rhamnopyranosyl, D-fucopyranosyl and D-talopyranosyl; O-aldo-hexopyranosyl-(1→4)-aldo-hexopyranosyl such as O-α-D-glucopyranosyl-(1→4)-D-glucopyranosyl(=D-maltosyl) and O-β-D-galactopyranosyl-(1→4)-D-glucopyranosyl (=D-lactosyl); and a group of the formula: —CH$_2$(CHOH)$_n$CH$_2$OH, such as 2-hydroxyethyl, 2,3-dihydroxy-n-propyl, 2,3,4-trihydroxy-n-butyl, 2,3,4,5-tetrahydroxy-n-pentyl and 2,3,4,5,6-pentahydroxy-n-hexyl. Within the scope of the invention, a preferred subgenus include compounds of formula [I] wherein $R^1$ is alkyl of one to five carbon atoms, alkenyl of three to four carbon atoms, alkynyl of three carbon atoms or 2-hydroxyethyl, and $R^2$ is D-aldo-pentofuranosyl, D- or L-aldo-pentopyranosyl, D- or L-aldo-hexopyranosyl, O-α-D-aldo-hexopyranosyl-(1→4)-D-aldo-hexopyranosyl or a group of the formula: —CH$_2$(CHOH)$_n$CH$_2$OH, wherein n is zero or an integer of one to four. Another preferred subgenus includes compounds of formula [I] in which $R^1$ is alkyl of one to five carbon atoms or alkenyl of three to four carbon atoms, and $R^2$ is D-glucopyranosyl, D-galactopyranosyl, D-mannopyranosyl, D-xylopyranosyl, L-arabinopyranosyl, O-α-D-glucopyranosyl-(1→4)-D-glucopyranosyl or a group of the formula: —CH₂(-CHOH)ₘ—CH₂OH, wherein m is an integer of one, two or four. A further preferred subgenus of the invention includes compounds of formula [I] in which R¹ is methyl, ethyl, n-propyl, isopropyl, n-butyl, isobutyl, n-pentyl, isopentyl, neopentyl, 2-n-propenyl, 2-methyl-2-n-propenyl, 2-n-butenyl or 3-n-butenyl, and R² is D-glucopyranosyl, D-galactopyranosyl, L-arabinopyranosyl, O-α-D-glucopyranosyl-(1→4)-D-glucopyranosyl, 2,3-dihydroxy-n-propyl or 2,3,4-trihydroxy-n-butyl. Further, the most preferred subgenus of the invention includes compounds of formula [I] in which R¹ is n-butyl, isobutyl or 2-methyl-2-n-propenyl, and R² is D-galactopyranosyl, L-arabinopyranosyl or O-α-D-glucopyranosyl-(1→4)-D-glucopyranosyl.

According to the present invention, the nitrosourea compound [I] is prepared by nitrosation of a compound having the formula:

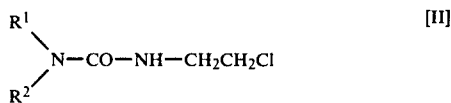

[II]

wherein R¹ and R² are the same as defined above.

The starting compound [II] is readily obtained. For example, it can be prepared by condensing a primary amine of the formula: R¹—NH₂ (wherein R¹ is the same as defined above) with a compound of the formula: R²—X (wherein R² is the same as defined above and X is hydroxyl or halogen) at about 20° to 80° C. in an inert solvent (e.g., methanol, ethanol) to give a secondary amine of the formula:

(wherein R¹ and R² are the same as defined above), and then condensing said secondary amine with 2-chloroethyl isocyanate at 0° to 30° C. in a suitable solvent (e.g., tetrahydrofuran, methanol, ethanol).

The nitrosation of the invention is accomplished by contacting the compound [II] with nitrous acid, nitrogen trioxide or nitrogen tetroxide in a suitable solvent. The reaction can be preferably carried out at a temperature of −20° to 20° C., especially at about 0° to about 5° C. Water, lower alkanols (e.g., methanol, ethanol), tetrahydrofuran, methylene chloride, ethyl acetate, acetic acid, formic acid and so forth are suitable as the inert solvent. When free nitrous acid is prepared by reacting an alkali metal salt of nitrous acid (e.g., sodium nitrite, potassium nitrite) or a lower alkyl ester thereof (e.g., butyl nitrite, amyl nitrite) with a mineral or organic acid (e.g., hydrochloric acid, sulfuric acid, formic acid, acetic acid and the like), it is preferred that said free nitrous acid is employed for the subsequent nitrosation reaction immediately after preparation thereof. On the other hand, when nitrogen trioxide or nitrogen tetroxide is employed in the invention, it is preferred to carry out the nitrosation reaction by dissolving the starting compound [II] in the suitable inert solvent and then introducing gaseous nitrogen trioxide or tetroxide thereto in the presence or absence of an acid acceptor. Sodium bicarbonate, sodium carbonate, potassium carbonate, sodium acetate, potassium acetate and the like are suitable as the acid acceptor. When the nitrosation reaction is completed, the compound [I] of the invention is readily recovered from the reaction mixture and may be, if required, further purified by silica gel chromatography.

The nitrosourea compound [I] thus obtained shows potent anti-tumor activity against various tumor cells such as Ehrlich's carcinoma, Sarcoma 180, Leukemia L-1210, Lewis lung carcinoma, Yoshida sarcoma, Rat ascites hepatoma and so forth. It may be useful to prolong the survival time of warm-blooded animals afflicted with said tumors and/or minimize the growth of said tumors in said animals. It may also be employed for therapy of malignant lymphoma, leukemia, stomach tumor, hepatoma and other malignant tumors. The nitrosourea compound [I] can be used for pharmaceutical use in the form of a pharmaceutical preparation suitable for either oral or parenteral administration. The compound [I] may also be used in conjunction or admixture with a pharmaceutical excipient. The excipient selected should be one which does not react with the compound [I]. Suitable excipients include, for example, gelatin, lactose, glucose, sodium chloride, starch, magnesium stearate, talcum, vegetable oil and so forth. Other known medicinal excipients may be employed. The pharmaceutical preparation may be a solid dosage form such as a tablet, a coated tablet, a pill or a capsule; or a liquid dosage form such as a solution, a suspension or an emulsion. Further, the compound [I] may be employed in the form of an injection or suppository when administered parenterally. The pharmaceutical preparation may be sterilized and/or may contain auxiliaries such as preserving and stabilizing agents. The dose of the compound (I) for pharmaceutical use depends on route of administration; the age, weight and condition of the host; and the particular disease to be treated. In general, it may be used for pharmaceutical use at a dose of 0.1 to 30 mg/kg, especially 0.2 to 10 mg/kg, per day.

Practical and presently-preferred embodiments of the present invention are illustratively shown in the following Examples. Throughout the specification, the terms "lower alkanol" and "lower alkyl" should be interpreted as referring to alkanol or alkyl of one to six carbon atoms.

EXAMPLE 1

(1) A mixture of 3.6 g of D-glucose and a 10% methylamine-methanol solution is heated at 60° C. for 20 minutes in a sealed tube. The reaction mixture is condensed to dryness under reduced pressure, whereby 3.8 g of 1-methylamino-1-deoxy-D-glucose are obtained as a crude product. 3.8 g of said crude product are dissolved in 40 ml of methanol, and a solution of 2.5 g of 2-chloroethyl isocyanate in 10 ml of tetrahydrofuran is added dropwise thereto at 0° to 5° C. The solution is stirred at the same temperature for 1.5 hours. Then, the reaction solution is condensed under reduced pressure, and a mixture of ethyl acetate and ether is added to the residue. 4.5 g of 1-(2-chloroethyl)-3-methyl-3-D-glucopyranosylurea are thereby obtained as colorless caramel.

IR$\nu_{max}^{nujol}$(cm⁻¹): 3300, 1630, 1530, 1070, 1030

NMR(D₂O) δ: 3.10(s, CH₃)

(2) 1.2 g of 1-(2-chloroethyl)-3-methyl-3-D-glucopyranosylurea are dissolved in 10 ml of formic acid, and 0.56 g of sodium nitrite is added thereto at 0° to 5° C. for one hour under stirring. The mixture is further stirred at the same temperature for 1.5 hours. After the reaction, the mixture is freeze-dried. The residue thus obtained is purified by silica gel chromatography(Solvent: chloroform-ethyl acetate-methanol(2:1:1)). 0.6 g of 1-(2-chloroethyl)-1-nitroso-3-methyl-3-D-glucopyranosylurea is thereby obtained as a pale yellow powder.

$[\alpha]_D^{26}$ −22.9°(C=1.1, methanol)
M.p. 69° C.(decomp.)
$IR\nu_{max}^{nujol}(cm^{-1})$: 3350, 1690, 1070
$NMR(D_2O)$ δ: 3.15(s, 3H, C$\underline{H}_3$), 4.20(t, 2H, —N(-NO)—C$\underline{H}_2$—)

EXAMPLE 2

3.0 g of 1-(2-chloroethyl)-3-methyl-3-D-glucopyranosylurea prepared in the same manner as described in Example 1-(1) are dissolved in a mixture of 80 ml of tetrahydrofuran and 80 ml of methylene chloride, and 15 g of sodium carbonate anhydrate are added thereto. 5 g of nitrogen tetroxide gas are introduced into the mixture for 10 minutes under ice-cooling. The mixture is further stirred at the same temperature for 10 minutes. After the reaction, 10 ml of methanol and 3 ml of water are added to the mixture, and the mixture is stirred for 10 minutes. Said mixture is dried, filtered and evaporated to remove solvent. Then, the residue obtained is purified by silica gel chromatography (Solvent: ethyl acetate-chloroform-methanol(5:2:1)). 2.4 g of 1-(2-chloroethyl)-1-nitroso-3-methyl-3-D-glucopyranosylurea are thereby obtained as a pale yellow powder.

M.p. 69° C.(decomp.)
$[\alpha]_D^{25}$ −22.9°(C=1.0, methanol)

EXAMPLE 3

(1) 3.6 g of D-glucose, 1.1 g of ethylamine and 2.5 g of 2-chloroethyl isocyanate are treated in the same manner as described in Example 1-(1). 5.5 g of 1-(2-chloroethyl)-3-ethyl-3-D-glucopyranosylurea are thereby obtained as colorless caramel.

$IR\nu_{max}^{nujol}(cm^{-1})$: 3350, 1640, 1535, 1080, 1040
$NMR(D_2O)$ δ: 1.25(t, CH$_2$—C$\underline{H}_3$)

(2) 6.0 g of 1-(2-chloroethyl)-3-ethyl-3-D-glucopyranosylurea are dissolved in 15 ml of formic acid, and 4.0 g of sodium nitrite are added gradually thereto at 0° to 5° C. for one hour under stirring. The mixture is further stirred at the same temperature for 20 minutes. 100 ml of ether-hexane(1:1) are added to the reaction mixture, and the resultant oil is collected therefrom. Said oil is washed with ether. Then, 100 ml of methylene chloride-methanol(5:1) are added to said oil, and insoluble materials are removed by filtration. The filtrate is evaporated to remove solvent, and the residue obtained is purified by silica gel chromatography (Solvent: chloroform-ethyl acetate-methanol (2:1:1)). 2.0 g of 1-(2-chloroethyl)-1-nitroso-3-ethyl-3-D-glucopyranosylurea are thereby obtained as pale yellow caramel.

$IR\nu_{max}^{liq}(cm^{-1})$: 3370, 1700, 1090
$NMR(D_2O)$ δ: 1.26(t, 3H, —C$\underline{H}_3$), 4.20(t, 2H, —N(-NO)—C$\underline{H}_2$—)
$[\alpha]_D^{20}$ +16.0°(C=0.4, methanol)

EXAMPLE 4

3.1 g of 1-(2-chloroethyl)-3-ethyl-3-D-glucopyranosylurea are dissolved in a mixture of 80 ml of tetrahydrofuran and 80 ml of methylene chloride, and 15 g of sodium carbonate anhydrate are added thereto. 5 g of nitrogen tetroxide gas are introduced into the mixture for 10 minutes under ice-cooling. The mixture is treated in the same manner as described in Example 2. 2.6 g of 1-(2-chloroethyl)-1-nitroso-3-ethyl-3-D-glucopyranosylurea are thereby obtained as pale yellow caramel.

$[\alpha]_D^{20}$ +16.0°(C=0.4, methanol)

EXAMPLE 5

(1) A mixture of 3.6 g of D-glucose, 1.3 g of n-propylamine and 15 ml of methanol is heated at 60° C. for 30 minutes. The reaction mixture is condensed to dryness under reduced pressure and the residue is washed with ether, whereby 4.4 g of 1-n-propylamino-1-deoxy-D-glucose are obtained as a crude product. 4.4 g of said crude product are dissolved in 50 ml of methanol and a solution of 2.5 g of 2-chloroethyl isocyanate in 10 ml of tetrahydrofuran is added dropwise thereto at 0° to 5° C. The solution is stirred at room temperature for one hour and the reaction solution is condensed under reduced pressure. The residue thus obtained is dissolved in 20 ml of formic acid and allowed to stand at room temperature for 20 minutes. 200 ml of ether-n-hexane mixture(1:1) is added to the solution and the resultant oily product is washed with ether repeatedly. 5.0 g of 1-(2-chloroethyl)-3-n-propyl-3-D-glucopyranosylurea are thereby obtained as brownish caramel, which can be, if desired, further purified by silica gel chromatography (Solvent: chloroform-ethyl acetate-methanol(1:2:1)) and obtained as colorless caramel.

$IR\nu_{max}^{nujol}(cm^{-1})$: 3300, 1630, 1530, 1080, 1040
$NMR(D_2O)$ δ: 0.93(t, 3H, C$\underline{H}_3$), 1.35–2.0(m, 2H, —C$\underline{H}_2$—CH$_3$)

(2) 4.5 g of 1-(2-chloroethyl)-3-n-propyl-3-D-glucopyranosylurea are dissolved in 20 ml of formic acid, and 2.8 g of sodium nitrite are added gradually thereto at 0° to 5° C. for one hour under stirring. The mixture is further stirred at the same temperature for one hour. After the reaction, 20 ml of methanol are added to the reaction mixture. Said mixture is neutralized with potassium carbonate under ice-cooling. Then, 150 ml of ethyl acetate are added to said mixture, and insoluble materials are removed by filtration. The filtrate is washed with an aqueous sodium bicarbonate solution, dried and evaporated to remove solvent. The residue thus obtained is purified by silica gel chromatography(Solvent: methanol-chloroform(1:5)). 1.5 g of 1-(2-chloroethyl)-1-nitroso-3-n-propyl-3-D-glucopyranosylurea are thereby obtained as pale yellow caramel.

$IR\nu_{max}^{CHCl_3}(cm^{-1})$: 3300, 1700, 1070
$NMR(D_2O)$ δ: 0.90(t, 3H, —C$\underline{H}_3$), 1.6–2.0(m, 2H, —C$\underline{H}_2$—CH$_3$), 4.20(t, 2H, —N(NO)—C$\underline{H}_2$—)
$[\alpha]_D^{26}$ +5.0°(C=1.5, methanol)

EXAMPLE 6

3.3 g of 1-(2-chloroethyl)-3-n-propyl-3-D-glucopyranosylurea are dissolved in a mixture of 60 ml of tetrahydrofuran and 60 ml of methylene chloride, and 15 g of sodium carbonate anhydrate are added thereto. 5 g of nitrogen tetroxide gas are introduced into the mixture for 10 minutes under ice-cooling. The mixture is treated in the same manner as described in Example 2. 2.6 g of 1-(2-chloroethyl)-1-nitroso-3-n-propyl-3-D-glucopyranosylurea are thereby obtained as yellow caramel.

$[\alpha]_D^{26}$ +5.0°(C=1.5, methanol)

EXAMPLE 7

(1) 3.6 g of D-glucose, 2.0 g of isopropylamine and 2.5 g of 2-chloroethyl isocyanate are treated in the same manner as described in Example 5-(1). 4.8 g of 1-(2-chloroethyl)-3-isopropyl-3-D-glucopyranosylurea are obtained as colorless caramel.

IR$\nu_{max}^{nujol}$(cm$^{-1}$): 3350, 1640, 1535, 1070, 1030
NMR(D$_2$O) δ: 1.38(d, —CH(C$\underline{H}$_3)$_2$)

(2) 6.0 g of 1-(2-chloroethyl)-3-isopropyl-3-D-glucopyranosylurea are dissolved in 50 ml of 10% hydrochloric acid, and 6 g of sodium nitrite are added gradually thereto at 0° to 5° C. under stirring. The mixture is further stirred at the same temperature for 10 minutes. The reaction mixture is extracted with ethyl acetate. The extract is washed with an aqueous sodium bicarbonate solution, dried and evaporated to remove solvent. Then, the residue thus obtained is purified by silica gel chromatography (Solvent: chloroform-methanol(5:1)). 2.0 g of 1-(2-chloroethyl)-1-nitroso-3-isopropyl-3-D-glucopyranosylurea are thereby obtained as pale yellow caramel.

IR$\nu_{max}^{CHCl_3}$(cm$^{-1}$): 3400, 1690, 1070
NMR(D$_2$O)δ: 1.35(d, 6H, —CH(C$\underline{H}$_3)$_2$), 4.10(t, 2H, —N(NO)—C$\underline{H}$_2—)
$[\alpha]_D^{25}$ +21.0°(C=1.2, methanol)

EXAMPLE 8

(1) 3.6 g of D-glucose, 1.7 g of n-butylamine and 2.5 g of 2-chloroethyl isocyanate are treated in the same manner as described in Example 5-(1). 5.0 g of 1-(2-chloroethyl)-3-n-butyl-3-D-glucopyranosylurea are obtained as colorless caramel.

IR$\nu_{max}^{nujol}$(cm$^{-1}$): 3300, 1630, 1530, 1070, 1030
NMR(D$_2$O) δ: 0.75-1.70(m, —C$\underline{H}$_2C$\underline{H}$_2CH$_3$)

(2) 2.2 g of 1-(2-chloroethyl)-3-n-butyl-3-D-glucopyranosylurea are dissolved in 10 ml of formic acid, and one g of sodium nitrite is added gradually thereto at 0° to 5° C. for 40 minutes under stirring. The mixture is further stirred at the same temperature for 1.5 hours. After the reaction, the mixture is treated in the same manner as described in Example 5-(2). 1.0 g of 1-(2-chloroethyl)-1-nitroso-3-n-butyl-3-D-glucopyranosylurea is thereby obtained as pale yellow caramel.

IR$\nu_{max}^{nujol}$(cm$^{-1}$): 3350, 1700, 1080
NMR(D$_2$O) δ: 0.70-1.80(m, 7H), 4.15(t, 2H), 5.10(d, 1H)
$[\alpha]_D^{26}$ +8.0°(C=0.8, methanol)

EXAMPLE 9

3.4 g of 1-(2-chloroethyl)-3-n-butyl-3-D-glucopyranosylurea are dissolved in a mixture of 60 ml of tetrahydrofuran and 60 ml of methylene chloride, and 15 g of sodium carbonate anhydrate are added thereto. 5 g of nitrogen tetroxide gas are introduced into the mixture for 10 minutes under ice-cooling. The mixture is treated in the same manner as described in Example 2. 2.9 g of 1-(2-chloroethyl)-1-nitroso-3-n-butyl-3-D-glucopyranosylurea are thereby obtained as yellow caramel.

$[\alpha]_D^{26}$ +8.0°(C=0.8, methanol)

EXAMPLE 10

(1) 3.6 g of D-glucose, 2.5 g of isobutylamine and 2.5 g of 2-chloroethyl isocyanate are treated in the same manner as described in Example 5-(1). 5.0 g of 1-(2-chloroethyl)-3-isobutyl-3-D-glucopyranosylurea are thereby obtained as colorless caramel.

IR$\nu_{max}^{nujol}$(cm$^{-1}$): 3350, 1635, 1535, 1070, 1030
NMR(D$_2$O) δ: 0.90(d, 6H, CH(C$\underline{H}$_3)$_2$), 1.7-2.3(m, 1H, —C$\underline{H}$(CH$_3$)$_2$)

(2) 3.4 g of 1-(2-chloroethyl)-3-isobutyl-3-D-glucopyranosylurea are dissoved in a mixture of 70 ml of tetrahydrofuran and 70 ml of methylene chloride, and 15 g of sodium carbonate anhydrate are added thereto. 5 g of nitrogen tetroxide gas are introduced into the mixture for 10 minutes under stirring and ice-cooling. The mixture is treated in the same manner as described in Example 2. 2.8 g of 1-(2-chloroethyl)-1-nitroso-3-isobutyl-3-D-glucopyranosylurea are thereby obtained as yellow caramel.

IR$\nu_{max}^{CHCl_3}$(cm$^{-1}$): 3400, 1700, 1080
NMR(D$_2$O) δ: 0.90(d, 6H, —CH)C$\underline{H}$_3)$_2$), 1.8-2.3(m, 1H, —C$\underline{H}$(CH$_3$)$_2$), 4.15(t, 2H, —N(NO)—C$\underline{H}$_2—)
$[\alpha]_D^{18}$ −12.1°(C=1.4, methanol)

EXAMPLE 11

(1) 3.6 g of D-glucose, 2.1 g of n-pentylamine and 2.5 g of 2-chloroethyl isocyanate are treated in the same manner as described in Example 5-(1). 6.5 g of 1-(2-chloroethyl)-3-n-pentyl-3-D-glucopyranosylurea are thereby obtained as brownish caramel.

IR$\nu_{max}^{CHCl_3}$(cm$^{-1}$): 3350, 1640, 1540, 1070
NMR(D$_2$O) δ: 0.70~2.00(m, —(C$\underline{H}$_2)$_3$C$\underline{H}$_3)

(2) 3.5 g of 1-(2-chloroethyl)-3-n-pentyl-3-D-glucopyranosylurea are dissolved in a mixture of 60 ml of tetrahydrofuran and 60 ml of methylene chloride, and 15 g of sodium carbonate anhydrate are added thereto. 5 g of nitrogen tetroxide gas are introduced into the mixture for 10 minutes under ice-cooling. The mixture is treated in the same manner as described in Example 2. 3.1 g of 1-(2-chloroethyl)-1-nitroso-3-n-pentyl-3-D-glucopyranosylurea are thereby obtained as yellow caramel.

IR$\nu_{max}^{CHCl_3}$(cm$^{-1}$): 3400, 1690, 1080
NMR(D$_2$O) δ: 0.70-2.00(m, 9H, —(C$\underline{H}$_2)$_3$C$\underline{H}$_3), 4.15(t, 2H, —N (NO)—C$\underline{H}$_2—)
$[\alpha]_D^{25}$ +3.3°(C=1.0, methanol)

EXAMPLE 12

(1) 3.6 g of D-glucose, 2.5 g of n-hexylamine and 2.5 g of 2-chloroethyl isocyanate are treated in the same manner as described in Example 5-(1). 6.8 g of 1-(2-chloroethyl)-3-n-hexyl-3-D-glucopyranosylurea are thereby obtained as brownish caramel.

IR$\nu_{max}^{CHCl_3}$(cm$^{-1}$): 3350, 1640, 1520, 1080, 1040

(2) 4.3 g of 1-(2-chloroethyl)-3-n-hexyl-3-D-glucopyranosylurea are dissolved in 15 ml of formic acid, and 2.4 g of sodium nitrite are added gradually thereto at 0° to 5° C. for one hour under stirring. The mixture is further stirred at the same temperature for 1.5 hours. After the reaction, the mixture is treated in the same manner as described in Example 5-(2). 1.8 g of 1-(2-chloroethyl)-1-nitroso-3-n-hexyl-3-D-glucopyranosylurea are thereby obtained as a yellow oil.

IR$\nu_{max}^{CHCl_3}$(cm$^{-1}$): 3400, 1700, 1495, 1080
NMR(CDCl$_3$) δ: 0.70-1.60(m, —(C$\underline{H}$_2)$_4$C$\underline{H}$_3),
$[\alpha]_D^{26}$ +4.4°(C=1.2, methanol)

EXAMPLE 13

3.7 g of 1-(2-chloroethyl)-3-n-hexyl-3-D-glucopyranosylurea are dissolved in a mixture of 60 ml of tetrahydrofuran and 60 ml of methylene chloride, and 15 g of sodium carbonate anhydrate are added thereto. 5 g of nitrogen tetroxide gas are introduced into the mixture for 10 minutes under ice-cooling. The mixture is treated in the same manner as described in Example 2. 3.1 g of 1-(2-chloroethyl)-1-nitroso-3-n-hexyl-3-D-glucopyranosylurea are thereby obtained as a yellow oil.

$[\alpha]_D^{26}+4.4°(C=1.2, \text{methanol})$

EXAMPLE 14

(1) 3.6 g of D-galoctose, 1.5 g of n-propylamine and 2.5 g of 2-chloroethyl isocyanate are treated in the same manner as described in Example 5-(1). 4.5 g of 1-(2-chloroethyl)-3-n-propyl-3-D-galactopyranosylurea are obtained as colorless caramel.

IR$\nu_{max}^{nujol}$(cm$^{-1}$): 3400, 1635, 1530, 1070, 1040

NMR(D$_2$O) δ: 0.95(t, 3H, C$\underline{H}_3$), 1.70–2.10(m, 2H, —C$\underline{H}_2$CH$_3$)

(2) 6.0 g of 1-(2-chloroethyl)-3-n-propyl-3-D-galactopyranosylurea are dissolved in 15 ml of formic acid, and 4.2 g of sodium nitrite are added gradually thereto at 0° to 5° C. for one hour under stirring. The mixture is further strirred at the same temperature for one hour. After the reaction, the mixture is treated in the same manner as described in Example 5-(2). 1.8 g of 1-(2-chloroethyl)-1-nitroso-3-n-propyl-3-D-galactopyranosylurea are thereby obtained as pale yellow caramel.

IR$\nu_{max}^{liq}$(cm$^{-1}$): 3380, 1690, 1080

NMR(D$_2$O) δ: 0.90(t, 3H, C$\underline{H}_3$), 1.60–2.00(m, 2H, —C$\underline{H}_2$—CH$_3$)

$[\alpha]_D^{23}+18.0°(C=1.0, \text{methanol})$

EXAMPLE 15

3.3 g of 1-(2-chloroethyl)-3-n-propyl-3-D-galactopyranosylurea are dissolved in a mixture of 60 ml of tetrahydrofuran and 60 ml of methylene chloride, and 15 g of sodium carbonate anhydrate are added thereto. 5 g of nitrogen tetroxide gas are introduced into the mixture for 10 minutes under ice-cooling. The mixture is treated in the same manner as described in Example 2. 2.8 g of 1-(2-chloroethyl)-1-nitroso-3-n-propyl-3-D-galactopyranosylurea are thereby obtained as pale yellow caramel. $[\alpha]_D^{23}+18.0°(C=1.0, \text{methanol})$

EXAMPLE 16

(1) 3.6 g of D-galactose, 2.4 g of isopropylamine and 2.5 g of 2-chloroethyl isocyanate are treated in the same manner as described in Example 5-(1). 5.0 g of 1-(2-chloroethyl)-3-isopropyl-3-D-galactopyranosylurea are thereby obtained as colorless caramel.

IR$\nu_{max}^{nujol}$(cm$^{-1}$): 3350, 1640, 1535, 1050

NMR(D$_2$O) δ: 1.38(d, —CH(C$\underline{H}_3$)$_2$)

(2) 6.0 g of 1-(2-chloroethyl)-3-isopropyl-3-D-galactopyranosylurea are dissolved in 20 ml of formic acid, and 4.2 g of sodium nitrite are added gradually thereto at 0° to 5° C. for one hour under stirring. The mixture is further stirred at the same temperature for one hour. After the reaction, the mixture is treated in the same manner as described in Example 5-(2). 1.8 g of 1-(2-chloroethyl)-1-nitroso-3-isopropyl-3-D-galactopyranosylurea are thereby obtained as pale yellow caramel.

IR$\nu_{max}^{CHCl_3}$(cm$^{-1}$): 3400, 1690, 1070

NMR(D$_2$O) δ: 1.40(d, 6H, —CH(C$\underline{H}_3$)$_2$), 4.16(t, 2H, —N(NO)—C$\underline{H}_2$—)

$[\alpha]_D^{20}+21.1°(C=0.9, \text{methanol})$

EXAMPLE 17

(1) 3.6 g of D-galactose, 1.8 g of n-butylamine and 2.5 g of 2-chloroethyl isocyanate are treated in the same manner as described in Example 5-(1). 5.2 g of 1-(2-chloroethyl)-3-n-butyl-3-D-galactopyranosylurea are thereby obtained as colorless caramel.

IR$\nu_{max}^{nujol}$(cm$^{-1}$): 3350, 1640, 1540, 1070, 1030

NMR(D$_2$O) δ: 0.8–1.90(m, (C$\underline{H}_2$)$_2$CH$_3$)

(2) 4.8 g of 1-(2-chloroethyl)-3-n-butyl-3-D-galactopyranosylurea are dissolved in 15 ml of formic acid, and 2.4 g of sodium nitrite are added gradually thereto at 0° to 5° C. for one hour under stirring. The mixture is further stirred at the same temperature for 1.5 hours. After the reaction, the mixture is treated in the same manner as described in Example 5-(2). 1.8 g of 1-(2-chloroethyl)-1-nitroso-3-n-butyl-3-D-galactopyranosylurea are thereby obtained as a yellow powder.

M.p. 44°–46.5° C.(decomp.)

IR$\nu_{max}^{CHCl_3}$(cm$^{-1}$): 3400, 1700, 1495, 1080

NMR(CDCl$_3$) δ: 0.80–1.90 (m, 7H, —(CH$_2$)$_2$CH$_3$), 4.20 (t, 2H, —N(NO)C$\underline{H}_2$—) $[\alpha]_D^{26}+16.4°(C=1.0, \text{methanol})$

EXAMPLE 18

3.4 g of 1-(2-chloroethyl)-3-n-butyl-3-D-galactopyranosulurea are dissolved in a mixture of 80 ml of tetrahydrofuran and 80 ml of methylene chloride, and 15 g of sodium carbonate anhydrate are added thereto. 5 g of nitrogen tetroxide gas are introduced into the mixture for 10 minutes under ice-cooling. The mixture is treated in the same manner as described in Example 2. 2.8 g of 1-(2-chloroethyl)-1-nitroso-3-n-butyl-3-D-galactopyranosylurea are thereby obtained as a yellow powder.

M.p. 44°–46.5° C.(decomp.)

EXAMPLE 19

(1) A mixture of 3.6 g of D-galactose, 2.0 g of isobutylamine and 2.5 g of 2-chloroethyl isocyanate are treated in the same manner as described in Example 5-(1). 5.5 g of 1-(2-chloroethyl)-3-isobutyl-3-D-galactopyranosylurea are thereby obtained as colorless caramel.

IR$\nu_{max}^{nujol}$(cm$^{-1}$): 3350, 1640, 1540, 1070

NMR(D$_2$O) δ: 0.93(d, 6H, —CH(C$\underline{H}_3$)$_2$), 1.75–2.20(m, 1H, —C$\underline{H}$(CH$_3$)$_2$)

(2) 7.0 g of 1-(2-chloroethyl)-3-isobutyl-3-D-galactopyranosylurea are dissolved in 15 ml of formic acid, and 5.0 g of sodium nitrite are added gradually thereto at 0° to 5° C. for one hour under stirring. The mixture is further stirred at the same temperature for one hour. After the reaction, the mixture is treated in the same manner as described in Example 5-(2). 2.0 g of 1-(2-chloroethyl)-1-nitroso-3-isobutyl-3-D-galactopyranosylurea are thereby obtained as a pale yellow powder.

M.p. 48°–53° C.

IR$\nu_{max}^{liq}$(cm$^{-1}$): 3380, 1695, 1090

NMR(CDCl$_3$) δ: 0.95(d, 6H, —CH(C$\underline{H}_3$)$_2$), 1.80–2.25(m, 1H, —C$\underline{H}$(CH$_3$)$_2$)

$[\alpha]_D^{23}-3.6°(C=1.0, \text{methanol})$

EXAMPLE 20

3.4 g of 1-(2-chloroethyl)-3-isobutyl-3-D-galactopyranosylurea are dissolved in a mixture of 80 ml of tetrahydrofuran and 80 ml of methylene chloride, and 15 g of sodium carbonate anhydrate are added thereto. 5 g of nitrogen tetroxide gas are introduced into the mixture for 10 minutes under ice-cooling. The mixture is treated in the same manner as described in Example 2. 3.0 g of 1-(2-chloroethyl)-1-nitroso-3-isobutyl-3-D-galactopyranosylurea are thereby obtained as a yellow powder.

M.p. 48°–53° C.

$[\alpha]_D^{25} - 3.4°(C=1.0, \text{methanol})$

EXAMPLE 21

(1) 3.6 g of D-galactose, 5 g of secondary butylamine and 3.0 g of 2-chloroethyl isocyanate are treated in the same manner as described in Example 5-(1). 4.5 g of 1-(2-chloroethyl)-3-sec.butyl-3-D-galactopyranosylurea are thereby obtained as pale brown caramel.

$IR\nu_{max}^{liq}(cm^{-1})$: 3360, 1630, 1535, 1050

NMR(D$_2$O) δ: 0.90(t, 3H, —CH$_2$—CH$_3$), 1.20(d, 3H, CH—CH$_3$), 1.30-1.75(m, 2H, —CH$_2$—CH$_3$)

(2) 7.0 g of 1-(2-chloroethyl)-3-sec.butyl-3-D-galactopyranosylurea are dissolved in 20 ml of formic acid, and 5.0 g of sodium nitrite are added gradually thereto at 0° to 5° C. for one hour under stirring. The mixture is further stirred at the same temperature for one hour. After the reaction, the mixture is treated in the same manner as described in Example 5-(2). 1.7 g of 1-(2-chloroethyl)-1-nitroso-3-sec.butyl-3-D-galactopyranosylurea are thereby obtained as pale yellow caramel.

$IR\nu_{max}^{liq}(cm^{-1})$: 3400, 1690, 1070

NMR(D$_2$O) δ: 0.90(t, 3H, —CH$_2$CH$_3$), 1.35(d, 3H, CH—CH$_3$), 1.55-2.00(m, 2H, —CH$_2$CH$_3$)

$[\alpha]_D^{20} + 13.8°(C=1.3, \text{methanol})$

EXAMPLE 22

(1) 3.6 g of D-galactose, 2.3 g of n-pentylamine and 2.5 g of 2-chloroethyl isocyanate are treated in the same manner as described in Example 5-(1). 5.5 g of 1-(2-chloroethyl)-3-n-pentyl-3-D-galactopyranosylurea are thereby obtained as colorless caramel.

$IR\nu_{max}^{CHCl3}(cm^{-1})$: 3350, 1640, 1535, 1060

NMR(D$_2$O) δ: 0.75-2.00(m, (CH$_2$)$_3$CH$_3$)

(2) 3.5 g of 1-(2-chloroethyl)-3-n-pentyl-3-D-galactopyranosylurea are dissolved in a mixture of 80 ml of tetrahydrofuran and 80 ml of methylene chloride, and 15 g of sodium carbonate anhydrate are added thereto. 5 g of nitrogen tetroxide gas are introduced into the mixture for 10 minutes under ice-cooling. The mixture is treated in the same manner as described in Example 2. 2.7 g of 1-(2-chloroethyl)-1-nitroso-3-n-pentyl-3-D-galactopyranosylurea are thereby obtained as yellow caramel.

$IR\nu_{max}^{CHCl3}(cm^{-1})$: 3400, 1690, 1090

NMR(D$_2$O) δ: 0.70-2.00(m, 9H, —(CH$_2$)$_3$CH$_3$), 4.15(t, 2H, —N(NO)CH$_2$—)

$[\alpha]_D^{25} + 11.4°(C=1.0, \text{methanol})$

EXAMPLE 23

(1) 3.6 g of D-galactose, 2.3 g of isopentylamine and 2.5 g of 2-chloroethyl isocyanate are treated in the same manner as described in Example 5-(1). 5.5 g of 1-(2-chloroethyl)-3-isopentyl-3-D-galactopyranosylurea are thereby obtained as colorless caramel.

$IR\nu_{max}^{CHCl3}(cm^{-1})$: 3350, 1640, 1535, 1060

NMR(D$_2$O) δ: 0.87(d, 6H, —CH(CH$_3$)$_2$), 1.20-2.00(m, 3H, —CH$_2$—CH(CH$_3$)$_2$)

(2) 3.5 g of 1-(2-chloroethyl)-3-isopentyl-3-D-galactopyranosylurea are dissolved in a mixture of 80 ml of tetrahydrofuran and 80 ml of methylene chloride, and 15 g of sodium carbonate anhydrate are added thereto. 5 g of nitrogen tetroxide gas are introduced into the mixture for 10 minutes under ice-cooling. The mixture is treated in the same manner as described in Example 2. 2.6 g of 1-(2-chloroethyl)-1-nitroso-3-isopentyl-3-D-galactopyranosylurea are thereby obtained as yellow caramel.

$IR\nu_{max}^{CHCl3}(cm^{-1})$: 3380, 1690, 1090

NMR(D$_2$O) δ: 0.89(d, 6H, —CH(CH$_3$)$_2$), 1.20-1.90(m, 3H, —CH$_2$—CH>)

$[\alpha]_D^{20} - 3.2°(C=1.0, \text{methanol})$

EXAMPLE 24

(1) 3.6 g of D-galactose, 3.5 g of neopentylamine and 2.5 g of 2-chloroethyl isocyanate are treated in the same manner as described in Example 5-(1). 5.0 g of 1-(2-chloroethyl)-3-neopentyl-3-D-galactopyranosylurea are thereby obtained as colorless caramel.

$IR\nu_{max}^{CHCl3}(cm^{-1})$: 3350, 1640, 1540, 1070

NMR(D$_2$O) δ: 0.90(s, —C(CH$_3$)$_3$), (2) 3.6 g of 1-(2-chloroethyl)-3-neopentyl-3-D-galactopyranosylurea are dissolved in a mixture of 60 ml of tetrahydrofuran and 60 ml of methylene chloride, and 15 g of sodium carbonate anhydrate are added thereto. 5 g of nitrogen tetroxide gas are introduced into the mixture for 10 minutes under ice-cooling. The mixture is treated in the same manner as described in Example 2. 2.9 g of 1-(2-chloroethyl)-1-nitroso-3-neopentyl-3-D-galactopyranosylurea are thereby obtained as yellow caramel.

$IR\nu_{max}^{CHCl3}(cm^{-1})$: 3400, 1705, 1075, 1045

NMR(D$_2$O) δ: 0.90(s, —C(CH$_3$)$_3$)

$[\alpha]_D^{19} + 48.7°(C=0.94, \text{methanol})$

EXAMPLE 25

(1) 3.6 g of D-galactose, 1.5 g of 2-propenylamine and 2.5 g of 2-chloroethyl isocyanate are treated in the same manner as described in Example 5-(1). 4.3 g of 1-(2-chloroethyl)-3-(2-propenyl)-3-D-galactopyranosylurea are obtained as colorless caramel. $IR\nu_{max}^{nujol}(cm^{-1})$: 3400, 1640, 1535, 1070

NMR: impossible to be assigned (2) 3.2 g of 1-(2-chloroethyl)-3-(2-propenyl)-3-D-galactopyranosylurea are dissolved in a mixture of 60 ml of tetrahydrofuran and 60 ml of methylene chloride, and 15 g of sodium carbonate anhydrate are added thereto. 5 g of nitrogen tetroxide gas are introduced into the mixture for 10 minutes under ice-cooling and stirring. The mixture is treated in the same manner as described in Example 2. 2.5 g of 1-(2-chloroethyl)-1-nitroso-3-(2-propenyl)-3-D-galactopyranosylurea are thereby obtained as yellow caramel.

$IR\nu_{max}^{CHCl3}(cm^{-1})$: 3400, 1700, 1090

$[\alpha]_D^{20} - 13.1°(C=1.1, \text{methanol})$

EXAMPLE 26

(1) 3.6 g of D-galactose, 1.4 g of 2-propynylamine and 2.5 g of 2-chloroethyl isocyanate are treated in the same manner as described in Example 5-(1). 4.3 g of 1-(2-chloroethyl)-3-(2-propynyl)-3-D-galactopyraosylurea are thereby obtained as colorless caramel.

$IR\nu_{max}^{nujol}(cm^{-1})$: 3350, 1640, 1535, 1050

NMR(D$_2$O) δ: 2.80 (m, —C≡CH)

(2) 3.2 g of 1-(2-chloroethyl)-3-(2-propynyl)-3-D-galactopyranosylurea are dissolved in a mixture of 60 ml of tetrahydrofuran and 60 ml of methylene chloride, and 15 g of sodium carbonate anhydrate are added thereto. 5 g of nitrogen tetroxide gas are introduced into the mixture for 10 minutes under ice-cooling and stirring. The mixture is treated in the same manner as described in Example 2. 2.5 g of 1-(2-chloroethyl)-1-nitroso-3-(2-propynyl)-3-D-galactopyranosylurea are thereby obtained as a pale yellow powder.

IR$\nu_{max}^{nujol}$(cm$^{-1}$): 3370, 3280, 1690, 1080

NMR(D$_2$O) δ: 2.75(m, 1H, —C≡C$\underline{H}$), 5.10(d, 1H, C$_1$—H)

$[\alpha]_D^{20}$ −9.2°(C=1.1, methanol)

EXAMPLE 27

(1) 3.0 g of D-ribose, 1.0 g of methylamine and 2.5 g of 2-chloroethyl isocyanate are treated in the same manner as described in Example 1-(1). 4.0 g of 1-(2-chloroethyl)-3-methyl-3-D-ribofuranosylurea are thereby obtained as colorless caramel.

IR$\nu_{max}^{nujol}$(cm$^{-1}$): 3350, 1635, 1540, 1050

NMR(D$_2$O) δ: 3.08(s, C$\underline{H}_3$)

(2) 2 g of 1-(2-chloroethyl)-3-methyl-3-D-ribofuranosylurea are dissolved in 10 ml of formic acid, and 1.1 g of sodium nitrite are added gradually thereto at 0° to 5° C. for one hour under stirring. The mixture is further stirred at the same temperature for one hour. After the reaction, the mixture is treated in the same manner as described in Example 1-(2). 1.4 g of 1-(2-chloroethyl)-1-nitroso-3-methyl-3-D-ribofuranosylurea are thereby obtained as a yellow powder.

M.p. 57°–60° C.(decomp.)

IR$\nu_{max}^{CHCl_3}$(cm$^{-1}$): 3400, 1690, 1060

NMR(CDCl$_3$) δ: 3.10(s, 3H, C$\underline{H}_3$), 5.30(d, 1H, C$_1$—H)

$[\alpha]_D^{26}$ −35.2°(C=1.1, methanol)

EXAMPLE 28

2.7 g of 1-(2-chloroethyl)-3-methyl-3-D-ribofuranosylurea are dissolved in a mixture of 80 ml of tetrahydrofuran and 80 ml of methylene chloride, and 15 g of sodium carbonate anhydrate are added thereto. 5 g of nitrogen tetroxide gas are introduced into the mixture for 10 minutes under ice-cooling. The mixture is treated in the same manner as described in Example 2. 2.1 g of 1-(2-chloroethyl)-1-nitroso-3-methyl-3-ribofuranosylurea are thereby obtained as a yellow powder.

M.p. 57°–60° C.(decomp.)

$[\alpha]_D^{26}$ −35.2°(C=1.1, methanol)

EXAMPLE 29

(1) 3.0 g of D-ribose, 1.9 g of n-butylamine and 2.5 g of 2-chloroethyl isocyanate are treated in the same manner as described in Example 5-(1). 5.0 g of 1-(2-chloroethyl)-3-n-butyl-3-D-ribofuranosylurea are thereby obtained as colorless caramel.

IR$\nu_{max}^{CHCl_3}$(cm$^{-1}$): 3350, 1640, 1535, 1060

NMR(D$_2$O) δ: 0.70–1.90(m, —(C$\underline{H}_2$)$_2$C$\underline{H}_3$)

(2) 3.1 g of 1-(2-chloroethyl)-3-n-butyl-3-D-ribofuranosylurea are dissolved in 10 ml of formic acid, and 1.5 g of sodium nitrite are added gradually thereto at 0° to 5° C. for one hour under stirring. The mixture is further stirred at the same temperature for one hour. After the reaction, the mixture is treated in the same manner as described in Example 5-(2). 1.4 g of 1-(2-chloroethyl)-1-nitroso-3-n-butyl-3-D-ribofuranosylurea are thereby obtained as yellow caramel.

IR$\nu_{max}^{liq}$(cm$^{-1}$): 3400, 1700, 1080

NMR(D$_2$O) δ: 0.70–2.00(m, 7H, —(C$\underline{H}_2$)$_2$C$\underline{H}_3$), 5.20(d, 1H, C$_1$—H)

$[\alpha]_D^{23}$ −3.0°(C=1.0, methanol)

EXAMPLE 30

(1) 3.6 g of D-mannose, 1.8 g of n-butylamine and 2.5 g of 2-chloroethyl isocyanate are treated in the same manner as described in Example 5-(1). 5.3 g of 1-(2-chloroethyl)-3-n-butyl-3-D-mannopyranosylurea are thereby obtained as colorless caramel.

IR$\nu_{max}^{nujol}$(cm$^{-1}$): 3350, 1640, 1540, 1070, 1030

NMR(D$_2$O) δ: 0.7–1.9(m, 7H, —(C$\underline{H}_2$)$_2$C$\underline{H}_3$), 5.1–5.3(m, 1H, C$_1$—H)

(2) 3.4 g of 1-(2-chloroethyl)-3-n-butyl-3-D-mannopyranosylurea are dissolved in a mixture of 60 ml of tetrahydrofuran and 60 ml of methylene chloride, and 15 g of sodium carbonate anhydrate are added thereto. 5 g of nitrogen tetroxide gas are introduced into the mixture for 10 minutes under ice-cooling. The mixture is treated in the same manner as described in Example 2. 2.9 g of 1-(2-chloroethyl)-1-nitroso-3-n-butyl-3-D-mannopyranosylurea are thereby obtained as yellow caramel.

IR$\nu_{max}^{CHCl_3}$(cm$^{-1}$): 3350, 1690, 1080

NMR(D$_2$O) δ: 0.8–2.0(m, 7H, —(C$\underline{H}_2$)$_2$C$\underline{H}_3$), 4.20(t, 2H, —N(NO)CH$_2$—)

$[\alpha]_D^{25}$ +33.1°(C=1.0, methanol)

EXAMPLE 31

5.4 g of 1-(2-chloroethyl)-3-n-butyl-3-D-mannopyranosylurea are dissolved in 20 ml of formic acid, and 3.5 g of sodium nitrite are added gradually thereto for 2 hours under ice-cooling and stirring. 40 ml of methanol and 30 g of potassium carbonate anhydrate are added to said mixture. Then, said mixture is further stirred for 10 minutes under ice-cooling. After the reaction, the mixture is treated in the same manner as described in Example 5-(2). 1.6 g of 1-(2-chloroethyl)-1-nitroso-3-n-butyl-3-D-mannopyranosylurea are thereby obtained as yellow caramel.

$[\alpha]_D^{26}$ +33.1°(C=1.2, methanol)

EXAMPLE 32

(1) 3.0 g of D-xylose, 1.5 g of n-propylamine and 2.5 g of 2-chloroethyl isocyanate are treated in the same manner as described in Example 5-(1). 4.0 g of 1-(2-chloroethyl)-3-n-propyl-3-D-xylopyranosylurea are thereby obtained as colorless caramel.

IR$\nu_{max}^{nujol}$(cm$^{-1}$): 3370, 1640, 1520, 1040

NMR(D$_2$O) δ: 0.85(t, 3H, C$\underline{H}_3$), 1.45–1.95(m, 2H, —C$\underline{H}_2$—CH$_3$)

(2) 9.0 g of 1-(2-chloroethyl)-3-n-propyl-3-D-xylopyranosylurea are dissolved in 25 ml of formic acid, and 6.0 g of sodium nitrite are added gradually thereto at 0° to 5° C. for one hour under stirring. The mixture is stirred at the same temperature for 30 minutes. After the reaction, the mixture is treated in the same manner as described in Example 5-(2). 3.7 g of 1-(2-chloroethyl)-1-nitroso-3-n-propyl-3-D-xylopyranosylurea are thereby obtained as pale yellow caramel.

IR$\nu_{max}^{CHCl_3}$(cm$^{-1}$): 3400, 1695, 1070

NMR(D$_2$O) δ: 0.85(t, 3H, C$\underline{H}_3$), 1.40–1.90(m, 2H, —C$\underline{H}_2$—CH$_3$), 4.15(t, 2H, —N(NO)—C$\underline{H}_2$—)

$[\alpha]_D^{20}$ +5.8°(C=1.6, methanol)

EXAMPLE 33

3.0 g of 1-(2-chloroethyl)-3-n-propyl-3-D-xylopyranosylurea are dissolved in a mixture of 80 ml of tetrahydrofuran and 80 ml of methylene chloride, and 15 g of sodium carbonate anhydrate are added thereto. 5 g of nitrogen tetroxide gas are introduced into the mixture for 10 minutes under ice-cooling. The mixture is treated in the same manner as described in Example 2. 2.6 g of 1-(2-chloroethyl)-1-nitroso-3-n-propyl-3-D-xylopyranosylurea are thereby obtained as yellow caramel.

$[\alpha]_D^{20} + 5.8°(C = 1.6, \text{methanol})$

EXAMPLE 34

(1) 3.0 g of D-xylose, 2.5 g of isopropylamine and 2.5 g of 2-chloroethyl isocyanate are treated in the same manner as described in Example 5-(1). 4.0 g of 1-(2-chloroethyl)-3-isopropyl-3-D-xylopyranosylurea are thereby obtained as colorless caramel.

IR$\nu_{max}^{CHCl_3}$(cm$^{-1}$): 3325, 1665, 1540, 1090
NMR(D$_2$) δ: 1.35(d, CH(C$\underline{H}_3$)$_2$)

(2) 3.0 g of 1-(2-chloroethyl)-3-isopropyl-3-D-xyloxypyranosylurea are dissolved in a mixture of 80 ml of tetrahydrofuran and 80 ml of methylene chloride, and 15 g of sodium carbonate anhydrate are added thereto. 5 g of nitrogen tetroxide gas are introduced into the mixture for 10 minutes under ice-cooling. The mixture is treated in the same manner as described in Example 2. 2.5 g of 1-(2-chloroethyl)-1-nitroso-3-D-xylopyranosylurea are thereby obtained as a yellow powder.

M.p. 50°–55° C. (decomp.)
IR$\nu_{max}^{CHCl_3}$(cm$^{-1}$): 3400, 1700, 1075
NMR(D$_2$O) δ: 1.35(d, 6H, CH(CH$_3$)$_2$), 4.15(t, 2H, —N(NO)—C$\underline{H}_2$—)
$[\alpha]_D^{25} + 22.2°(C = 1.0, \text{methanol})$

EXAMPLE 35

(1) 3.0 g of L-arabinose, 1.5 g of n-propylamine and 2.5 g of 2-chloroethyl isocyanate are treated in the same manner as described in Example 5-(1). 4.1 g of 1-(2-chloroethyl)-3-n-propyl-3-L-arabinopyranosylurea are thereby obtained as colorless caramel.

IR$\nu_{max}^{nujol}$(cm$^{-1}$): 3400, 1645, 1540, 1070
NMR(D$_2$O) δ: 0.90(t, 3H, C$\underline{H}_3$), 1.40–1.90(m, 2H, —C$\underline{H}_2$—CH$_3$)

(2) 9.0 g of 1-(2-chloroethyl)-3-n-propyl-3-L-arabinopyraosylurea are dissolved in 25 ml of formic acid, and 6.0 g of sodium nitrite are added gradually thereto at 0° to 5° C. for one hour under stirring. The mixture is stirred at the same temperature for 30 minutes. After the reaction, the mixture is treated in the same manner as described in Example 5-(2). 3.5 g of 1-(2-chloroethyl)-1-nitroso-3-n-propyl-3-L-arabinopyranosylurea are thereby obtained as pale yellow caramel.

IR$\nu_{max}^{CHCl_3}$(cm$^{-1}$): 3400, 1695, 1080
NMR(D$_2$O) δ: 0.90(t, 3H, —C$\underline{H}_3$), 1.40–1.90(m, 2H, —C$\underline{H}_2$—CH$_3$)
$[\alpha]_D^{20} + 44.5°(C = 1.2, \text{methanol})$

EXAMPLE 36

3.0 g of 1-(2-chloroethyl)-3-n-propyl-3-L-arabinopyranosylurea are dissolved in a mixture of 80 ml of tetrahydrofuran and 80 ml of methylene chloride, and 15 g of sodium carbonate are added thereto. 5 g of nitrogen tetroxide gas are introduced into the mixture for 10 minutes under ice-cooling. The mixture is treated in the same manner as described in Example 2. 2.5 g of 1-(2-chloroethyl)-1-nitroso-3-n-propyl-3-L-arabinopyranosylurea are thereby obtained as yellow caramel.

$[\alpha]_D^{20} + 44.5°(C = 1.2, \text{methanol})$

EXAMPLE 37

(1) 3.0 g of L-arabinose, 2.5 g of isopropylamine and 2.5 g of 2-chloroethyl isocyanate are treated in the same manner as described in Example 5-(1). 4.2 g of 1-(2-chloroethyl)-3-isopropyl-3-L-arabinopyranosylurea are thereby obtained as colorless caramel.

IR$\nu_{max}^{CHCl_3}$(cm$^{-1}$): 3350, 1660, 1540, 1090
NMR(D$_2$O) δ: 1.35(d, CH(C$\underline{H}_3$)$_2$)

(2) 3.0 g of 1-(2-chloroethyl)-3-isopropyl-3-L-arabinopyranosylurea are dissolved in a mixture of 80 ml of tetrahydrofuran and 80 ml of methylene chloride, and 15 g of sodium carbonate anhydrate are added thereto. 5 g of nitrogen tetroxide gas are introduced into the mixture for 10 minutes under ice-cooling. The mixture is treated in the same manner as described in Example 2. 2.4 g of 1-(2-chloroethyl)-1-nitroso-3-isopropyl-3-L-arabinopyranosylurea are thereby obtained as yellow caramel.

IR$\nu_{max}^{CHCl_3}$(cm$^{-1}$): 3400, 1695, 1080
NMR(D$_2$O) δ: 1.35(d, 6H, CH(CH$_3$)$_2$), 4.15(t, 2H, —N(NO)C$\underline{H}_2$—)
$[\alpha]_D^{29} + 64.4°(C = 1.0, \text{methanol})$

EXAMPLE 38

(1) 3.0 g of L-arabinose, 1.8 g of isobutylamine and 2.5 g of 2-chloroethyl isocyanate are treated in the same manner as described in Example 5-(1). 4.3 g of 1-(2-chloroethyl)-3-isobutyl-3-L-arabinopyranosylurea are thereby obtained as colorless caramel.

IR$\nu_{max}^{CHCl_3}$(cm$^{-1}$): 3360, 1630, 1540, 1090
NMR(D$_2$O) δ: 0.90(d, 6H, CH(C$\underline{H}_3$)$_2$), 1.90–2.30(m, 1H, —C$\underline{H}$(CH$_3$)$_2$)

(2) 3.1 g of 1-(2-chloroethyl)-3-isobutyl-3-L-arabinopyranosylurea are dissolved in a mixture of 60 ml of tetrahydrofuran and 60 ml of methylene chloride, and 15 g of sodium carbonate anhydrate are added thereto. 5 g of nitrogen tetroxide gas are introduced into the mixture for 10 minutes under ice-cooling. The mixture is treated in the same manner as described in Example 2. 2.3 g of 1-(2-chloroethyl)-1-nitroso-3-isobutyl-3-L-arabinopyranosylurea are thereby obtained as pale yellow caramel.

IR$\nu_{max}^{liq}$(cm$^{-1}$): 3400, 1690, 1080
NMR(D$_2$O) δ: 0.95(d, 6H, —CH(C$\underline{H}_3$)$_2$), 1.90–2.40(m, 1H, —C$\underline{H}$(CH$_3$)$_2$), 4.10(t, 2H, —N(NO)—C$\underline{H}_2$—)
$[\alpha]_D^{20} + 28.0°(C = 1.4, \text{methanol})$

EXAMPLE 39

(1) 4.5 g of L-arabinose, 2.5 g of 2-propenylamine and 3.5 g of 2-chloroethyl isocyanate are treated in the same manner as described in Example 5-(1). 5.5 g of 1-(2-chloroethyl)-3-(2-propenyl)-3-L-arabinopyranosylurea are thereby obtained as colorless powder.

IR$\nu_{max}^{nujol}$(cm$^{-1}$): 3340, 1630, 1530, 1080
NMR(D$_2$O) δ: 5.0–6.3(m, 4H, —C$\underline{H}$=C$\underline{H}_2$, C$_1$—H)

(2) 3.2 g of 1-(2-chloroethyl)-3-(2-propenyl)-3-L-arabinopyranosylurea are dissolved in a mixture of 60 ml of tetrahydrofuran and 60 ml of methylene chloride, and 15 g of sodium carbonate anhydrate are added thereto. 5 g of nitrogen tetroxide gas are introduced into the mixture for 10 minutes under ice-cooling and stirring. The mixture is treated in the same manner as described in Example 2. 2.3 g of 1-(2-chloroethyl)-1- nitroso-3-(2-propenyl)-3-L-arabinopyranosylurea are thereby obtained as yellow caramel.

IR$\nu_{max}^{CHCl_3}$(cm$^{-1}$): 3400, 1700, 1080

NMR(D$_2$O) δ: 4.9–6.3(m, 4H, —C$\underline{H}$=C$\underline{H}_2$, C$_1$—H)

$[\alpha]_D^{20}$ +12.8°(C=1.3, methanol)

EXAMPLE 40

(1) 3.3 g of L-rhamnose, 1.8 g of n-butylamine and 2.5 g of 2-chloroethyl isocyanate are treated in the same manner as described in Example 5-(1). 4.2 g of 1-(2-chloroethyl)-3-n-butyl-3-L-rhamnopyranosylurea are thereby obtained as colorless caramel.

IR$\nu_{max}^{nujol}$(cm$^{-1}$): 3350, 1640, 1530, 1070

(2) 3.2 g of 1-(2-chloroethyl)-3-n-butyl-3-L-rhamnopyranosylurea are dissolved in 10 ml of formic acid, and 1.5 g of sodium nitrite are added gradually thereto at 0° to 5° C. for one hour under stirring. The mixture is further stirred at the same temperature for one hour. After the reaction, the mixture is treated in the same manner as described in Example 5-(2). 0.8 g of 1-(2-chloroethyl)-1-nitroso-3-n-butyl-3-L-rhamnopyranosylurea is thereby obtained as yellow caramel.

IR$\nu_{max}^{nujol}$(cm$^{-1}$): 3350, 1700, 1070

NMR(D$_2$O) δ: 0.70–2.00(m, (C$\underline{H}_2$)$_2$C$\underline{H}_3$), accompanied by methyl protons (1.1 ppm, d)

$[\alpha]_D^{26}$ −20.1°(C=1.4, methanol)

EXAMPLE 41

3.2 g of 1-(2-chloroethyl)-3-n-butyl-3-L-rhamnopyranosylurea are dissolved in a mixture of 60 ml of tetrahydrofuran and 60 ml of methylene chloride, and 15 g of sodium carbonate are added thereto. 5 g of nitrogen tetroxide gas are introduced into the mixture for 10 minutes under ice-cooling. The mixture is treated in the same manner as described in Example 2. 3.5 g of 1-(2-chloroethyl)-1-nitroso-3-n-butyl-3-L-rhamnopyranosylurea are thereby obtained as yellow caramel.

$[\alpha]_D^{26}$ −20.1°(C=1.4, methanol)

EXAMPLE 42

(1) A mixture of 7.2 g of D-maltose monohydrate, 0.9 g of methylamine and 20 ml of methanol is heated at 60° C. for one hour in a sealed tube. The reaction mixture is condensed to dryness under reduced pressure and the residue is washed with ether, whereby 7.1 g of [O-α-D-glucopyranosyl-(1→4)-D-glucopyranosyl]-methylamine (i.e., 1-methylamino-1-deoxy-D-maltose) are obtained as a crude product, 7.1 g of said crude product are dissolved in 50 ml of methanol, and a solution of 2.5 g of 2-chloroethyl isocyanate in 10 ml of tetrahydrofuran is added thereto at 0° to 5° C. The resulting solution is stirred at room temperature for 1.5 hours. Then, the reaction solution is condensed under reduced pressure, and a mixture of ethyl acetate and ether is added to the residue. 7.4 g of 1-(2-chloroethyl)-3-methyl-3-[O-α-D-glucopyranosyl-(1→4)-D-glucopyranosyl]urea(i.e., 1-(2-chloroethyl)-3-methyl-3-D-maltosylurea) are thereby obtained as a colorless amorphous powder.

IR$\nu_{max}^{nujol}$(cm$^{-1}$): 3350, 1640, 1535, 1070, 1030

NMR(D$_2$O) δ: 3.15(s, C$\underline{H}_3$)

(2) 3.0 g of 1-(2-chloroethyl)-3-methyl-3-[O-α-D-glucopyranosyl-(1→4)-D-glucopyranosyl]urea are dissolved in 10 ml of formic acid, and 1.0 g of sodium nitrite is added gradually thereto at 0° to 5° C. for 40 minutes under stirring. The mixture is further stirred at the same temperature for 1.5 hours. After the reaction, the mixture is treated in the same manner as described in Example 1-(2)(Solvent used for the chromatography: chloroform-ethyl acetate-methanol (1:1:1)). 1.0 g of 1-(2-chloroethyl)-1-nitroso-3-methyl-3-[O-α-D-glucopyranosyl-(1→4)-D-glucopyranosyl]urea (i.e., 1-(2-chloroethyl)-1-nitroso-3-methyl-D-maltosylurea) is thereby obtained as a pale yellow powder.

M.p. 66°–70° C.(decomp.)

IR$\nu_{max}^{nujol}$(cm$^{-1}$): 3300, 1700, 1070, 1030

NMR(D$_2$O) δ: 3.12(s, 3H, —C$\underline{H}_3$), 4.15(t, 2H, —N(NO)—C$\underline{H}_2$—)

$[\alpha]_D^{26}$ +42.9°(C=1.2, methanol)

EXAMPLE 43

4.6 g of 1-(2-chloroethyl)-3-methyl-3-[O-α-D-glucopyranosyl-(1→4)-D-glucopyranosyl]urea are dissolved in a mixture of 170 ml of tetrahydrofuran and 30 ml of acetic acid, and 20 g of sodium acetate anhydrate are added thereto. 8 g of nitrogen tetroxide gas are introduced into the mixture for 10 minutes under ice-cooling and stirring. The mixture is further stirred at the same temperature for 20 minutes. After the reaction, 200 ml of n-hexane are added to the mixture, and the resulting mixture is filtered. The filtrate is evaporated to remove solvent. 200 ml of methanol-ether(1:20) are added to the residue thus obtained, and the resultant oily product is purified by silica gel chromatography (Solvent: ethyl acetate-chloroform-methanol(2:1:1). 3.35 g of 1-(2-chloroethyl)-1-nitroso-3-methyl-3-[O-α-D-glucopyranosyl-(1→4)-D-glucopyranosyl]urea (i.e., 1-(2-chloroethyl)-1-nitroso-3-methyl-3-D-maltosylurea) are thereby obtained as a pale yellow powder.

M.p. 66°–70° C.(decomp.)

$[\alpha]_D^{26}$ +42.9°(C=1.2, methanol)

EXAMPLE 44

(1) 7.2 g of D-maltose monohydrate, 1.5 g of n-propylamine and 2.5 g of 2-chloroethyl isocyanate are treated in the same manner as described in Example 42-(1). 8.5 g of 1-(2-chloroethyl)-3-n-propyl-3-[O-α-D-glucopyranosyl-(1→4)-D-glucopyranosyl]urea (i.e., 1-(2-chloroethyl)-3-n-propyl-3-D-maltosylurea) are thereby obtained as a colorless amorphous powder.

IR$\nu_{max}^{nujol}$(cm$^{-1}$): 3350, 1640, 1535, 1070

NMR(D$_2$O) δ: 0.90(t, 3H, C$\underline{H}_3$), 1.40–1.90(m, 2H, —C$\underline{H}_2$—CH$_3$)

(2) 5.0 g of 1-(2-chloroethyl)-3-n-propyl-3-[O-α-D-glucopyranosyl-(1→4)-D-glucopyranosyl]urea are dissolved in 20 ml of formic acid, and 1.5 g of sodium nitrite are added gradually thereto at 0° to 5° C. for one hour under stirring. The mixture is further stirred at the same temperature for 1.5 hours. After the reaction, the mixture is treated in the same manner as described in Example 1-(2) (Solvent used for the chromatography: chloroform-ethyl acetate-methanol (1:2:1)). 0.8 g of 1-(2-chloroethyl)-1-nitroso-3-n-propyl-3-[O-α-D-glucopyranosyl-(1→4)-D-glucopyranosyl]urea (i.e., 1-(2-chloroethyl)-1-nitroso-3-n-propyl-3-D-maltosylurea) is thereby obtained as a pale yellow powder.

M.p. 59°–62° C.(decomp.)

IR$\nu_{max}^{KBr}$(cm$^{-1}$): 3380, 1690, 1050

NMR(D$_2$O) δ: 0.91(t, 3H, CH$_3$), 1.4–1.9(m, 2H, —C$\underline{H}_2$—CH$_3$), 4.20(t, 2H, —N(NO)—C$\underline{H}_2$—)

$[\alpha]_D^{26}$ +62.9°(C=1.0, methanol)

EXAMPLE 45

4.8 g of 1-(2-chloroethyl)-3-n-propyl-3-[O-α-D-glucopyranosyl-(1→4)-D-glucopyranosyl]urea are dissolved in a mixture of 170 ml of tetrahydrofuran and 30 ml of acetic acid, and 20 g of sodium acetate anhydrate are added thereto. 8 g of nitrogen tetroxide gas are introduced into the mixture for 10 minutes under ice-cooling and stirring. The mixture is treated in the same manner as described in Example 43. 3.6 g of 1-(2-chloroethyl)-1-nitroso-3-n-propyl-3-[O-α-D-glucopyranosyl-(1→4)-D-glucopyranosyl]urea (i.e., 1-(2-chloroethyl)-1-nitroso-3-n-propyl-3-D-maltosylurea) are thereby obtained as a pale yellow powder.

M.p. 59°-62° C.(decomp.)
$[\alpha]_D^{26} + 62.9°(C=1.0, \text{methanol})$

EXAMPLE 46

(1) 7.2 g of D-maltose monohydrate, 2.0 g of isopropylamine and 2.5 g of 2-chloroethyl isocyanate are treated in the same manner as described in Example 42-(1). 7.2 g of 1-(2-chloroethyl)-3-isopropyl-3-[O-α-D-glucopyranosyl-(1→4)-D-glucopyranosyl]urea (i.e., 1-(2-chloroethyl)-3-isopropyl-3-D-maltosylurea) are thereby obtained as a colorless amorphous powder.

IR$\nu_{max}^{nujol}$(cm$^{-1}$): 3350, 1620, 1540, 1070, 1040
NMR(D$_2$O) δ: 1.20(d, —CH(C$\underline{H}_3$)$_2$)

(2) 4.8 g of 1-(2-chloroethyl)-3-isopropyl-3-[O-α-D-glucopyranosyl-(1→4)-D-glucopyranosyl]urea are dissolved in a mixture of 170 ml of tetrahydrofuran and 30 ml of acetic acid, and 20 g of sodium acetate anhydrate are added thereto. 8 g of nitrogen tetroxide gas are introduced into the mixture for 10 minutes under ice-cooling and stirring. The mixture is treated in the same manner as described in Example 43. 3.6 g of 1-(2-chloroethyl)-1-nitroso-3-isopropyl-3-[O-α-D-glucopyranosyl-(1→4)-D-glucopyranosyl]urea (i.e., 1-(2-chloroethyl)-1-nitroso-3-isopropyl-3-D-maltosylurea) are thereby obtained as a pale yellow powder.

M.p. 66°-71° C.(decomp.)
IR$\nu_{max}^{nujol}$(cm$^{-1}$): 3400, 1700, 1080, 1040
NMR(D$_2$O) δ: 1.36(d, 6H, —CH(C$\underline{H}_3$)$_2$), 4.15(t, 2H, —N(NO)—C$\underline{H}_2$—)
$[\alpha]_D^{25} + 70.5°(C=1.0, \text{methanol})$

EXAMPLE 47

(1) 7.2 g of D-maltose monohydrate, 2.2 g of n-butylamine and 2.5 g of 2-chloroethyl isocyanate are treated in the same manner as described in Example 42-(1). 8.0 g of 1-(2-chloroethyl)-3-n-butyl-3-[O-α-D-glucopyranosyl-(1→4)-D-glucopyranosyl]urea (i.e., 1-(2-chloroethyl)-3-n-butyl-3-D-maltosylurea) are thereby obtained as a colorless powder.

M.p. 91°-95° C.(decomp.)
IR$\nu_{max}^{nujol}$(cm$^{-1}$): 3350, 1640, 1540, 1070, 1030
NMR(D$_2$O) δ: 0.7-2.0(m, —(C$\underline{H}_2$)$_2$C$\underline{H}_3$)

(2) 4.5 g of 1-(2-chloroethyl)-3-n-butyl-3-[O-α-D-glucopyranosyl-(1→4)-D-glucopyranosyl]urea are dissolved in 10 ml of formic acid, and 1.5 g of sodium nitrite are added gradually thereto at 0° to 5° C. for 50 minutes under stirring. The mixture is further stirred at the same temperature for 1.5 hours. After the reaction, the mixture is treated in the same manner as described in Example 1-(2). 1.4 g of 1-(2-chloroethyl)-1-nitroso-3-n-butyl-3-[O-α-D-glucopyranosyl-(1→4)-D-glucopyranosyl]urea (i.e., 1-(2-chloroethyl)-1-nitroso-3-n-butyl-3-D-maltosylurea) are thereby obtained as a pale yellow powder.

M.p. 76°-80° C.(decomp.)
IR$\nu_{max}^{nujol}$(cm$^{-1}$): 3350, 1700, 1070, 1030
NMR(D$_2$O) δ: 0.70-1.90(m, 7H, (C$\underline{H}_2$)$_2$C$\underline{H}_3$), 4.25(t, 2H, —N(NO)C$\underline{H}_2$—)
$[\alpha]_D^{26} + 61.5°(C=1.7, \text{methanol})$

EXAMPLE 48

4.9 g of 1-(2-chloroethyl)-3-n-butyl-3-[O-α-D-glucopyranosyl-(1→4)-D-glucopyranosyl]urea are dissolved in a mixture of 150 ml of tetrahydrofuran and 30 ml of acetic acid, and 20 g of sodium acetate anhydrate are added thereto. 8 g of nitrogen tetroxide gas are introduced into the mixture for 10 minutes under ice-cooling and stirring. The mixture is treated in the same manner as described in Example 43. 3.8 g of 1-(2-chloroethyl)-1-nitroso-3-n-butyl-3-[O-α-D-glucopyranosyl-(1→4)-D-glucopyranosyl]urea (i.e., 1-(2-chloroethyl)-1-nitroso-3-n-butyl-3-D-maltosylurea) are thereby obtained as a pale yellow powder.

M.p. 76°-80° C.(decomp.)
$[\alpha]_D^{26} + 61.5°(C=1.7, \text{methanol})$

EXAMPLE 49

(1) 7.2 g of D-maltose monohydrate, 2.9 g of isobutylamine and 2.5 g of 2-chloroethyl isocyanate are treated in the same manner as described in Example 42-(1). 8.0 g of 1-(2-chloroethyl)-3-isobutyl-3-[O-α-D-glucopyranosyl-(1→4)-D-glucopyranosyl]urea (i.e., 1-(2-chloroethyl)-3-isobutyl-3-D-maltosylurea) are thereby obtained as a colorless powder.

M.p. 86°-90° C.(decomp.)
IR$\nu_{max}^{nujol}$(cm$^{-1}$): 3350, 1635, 1540, 1080, 1030
NMR(D$_2$O) δ: 0.91(d, 6H, —CH(C$\underline{H}_3$)$_2$), 1.80-2.25(m, 1H, —C$\underline{H}$(CH$_3$)$_2$)
$[\alpha]_D^{20} + 72.3°(C=0.8, \text{methanol})$ (2) 4.9 g of 1-(2-chloroethyl)-3-isobutyl-3-[O-α-D-glucopyranosyl-(1→4)-D-glucopyranosyl]urea are dissolved in a mixture of 150 ml of tetrahydrofuran and 20 ml of acetic acid, and 20 g of sodium acetate anhydrate are added thereto. 8 g of nitrogen tetroxide gas are introduced into the mixture for 10 minutes under ice-cooling and stirring. The mixture is treated in the same manner as described in Example 43. 2.5 g of 1-(2-chloroethyl)-1-nitroso-3-isobutyl-3-[O-α-D-glucopyranosyl-(1→4)-D-glucopyranosyl]urea (i.e., 1-(2-chloroethyl)-1-nitroso-3-isobutyl-3-D-maltosylurea) are thereby obtained as a yellow powder.

M.p. 69°-74° C.(decomp.)
IR$\nu_{max}^{nujol}$(cm$^{-1}$): 3350, 1695, 1080, 1040
NMR(D$_2$O) δ: 0.90(d, 6H, —CH(C$\underline{H}_3$)$_2$), 1.80-2.25(m, 1H, —C$\underline{H}$(CH$_3$)$_2$), 4.20(t, 2H, —N(NO)—C$\underline{H}_2$—)
$[\alpha]_D^{20} + 51.7°(C=2.5, \text{methanol})$

EXAMPLE 50

(1) 7.2 g of D-maltose monohydrate, 2.5 g of n-pentylamine and 2.5 g of 2-chloroethyl isocyanate are treated in the same manner as described in Example 42-(1). 8.1 g of 1-(2-chloroethyl)-3-n-pentyl-3-[O-α-D-glucopyranosyl-(1→4)-D-glucopyranosyl]urea (i.e., 1-(2-chloroethyl)-3-n-pentyl-3-D-maltosylurea) are thereby obtained as a colorless powder.

IR$\nu_{max}^{nujol}$(cm$^{-1}$): 3350, 1640, 1540, 1070
NMR(D$_2$O) δ: 0.7-1.0(m, 3H, C$\underline{H}_3$), 1.0-2.0(m, 6H, —C$\underline{H}_2$C$\underline{H}_2$C$\underline{H}_2$—CH$_3$)

(2) 5.2 g of 1-(2-chloroethyl)-3n-pentyl-3-[O-α-D-glucopyranosyl-(1→4)-D-glucopyranosyl]urea are dissolved in 20 ml of formic acid, and 2 g of sodium nitrite are added gradually thereto at 0° to 5° C. for one hour under stirring. The mixture is further stirred at the same temperature for 1.5 hours. After the reaction, the mixture is treated in the same manner as described in Example 1-(2). 1.0 g of 1-(2-chloroethyl)-1-nitroso-3-n-pentyl- 3-[O-α-D-glucopyranosyl-(1→4)-D-glucopyranosyl-]urea (i.e., 1-(2-chloroethyl)-1-nitroso-3-n-pentyl-3-D-maltosylurea) is thereby obtained as a pale yellow powder.

M.p. 71°–75° C.(decomp.)
IR$\nu_{max}^{KBr}$(cm$^{-1}$): 3370, 1685, 1050
NMR(D$_2$O) δ: 0.7–1.0(m, 3H, CH$_3$), 1.0–2.0(m, 6H, —CH$_2$CH$_2$CH$_2$—CH$_3$), 4.15(t, 2H, —N(NO)—CH$_2$—)
[α]$_D^{26}$+58.4°(C=0.8, methanol)

EXAMPLE 51

5.1 g of 1-(2-chloroethyl)-3-n-pentyl-3-[O-α-D-glucopyranosyl-(1→4)-D-glucopyranosyl]urea are dissolved in a mixture of 150 ml of tetrahydrofuran and 20 ml of acetic acid, and 20 g of sodium acetate anhydrate are added thereto. 8 g of nitrogen tetroxide gas are introduced into the mixture for 10 minutes under ice-cooling and stirring. The mixture is treated in the same manner as described in Example 43. 3.8 g of 1-(2-chloroethyl)-1-nitroso-3-n-pentyl-3-[O-α-D-glucopyranosyl-(1→4)-D-glucopyranosyl]urea (i.e., 1-(2-chloroethyl)-1-nitroso-3-n-pentyl-3-D-maltosylurea) are thereby obtained as pale yellow powder.

M.p. 71°–75°(decomp.)
[α]$_D^{26}$+58.4°(C=0.8, methanol)

EXAMPLE 52

(1) 7.2 g of D-maltose monohydrate, 3.0 g of n-hexylamine and 2.5 g of 2-chloroethyl isocyanate are treated in the same manner as described in Example 42-(1). 8.3 g of 1-(2-chloroethyl)-3-n-hexyl-3-[O-α-D-glucopyranosyl-(1→4)-D-glucopyranosyl]urea (i.e., 1-(2-chloroethyl)-3-n-hexyl-3-D-maltosylurea) are thereby obtained as a colorless powder.

IR$\nu_{max}^{nujol}$(cm$^{-1}$): 3350, 1640, 1540, 1070, 1030
NMR(d$_2$O) δ: 0.70–2.10(m, —(CH$_2$)$_4$CH$_3$)

(2) 5.2 g of 1-(2-chloroethyl)-3-n-hexyl-3-[O-α-D-glucopyranosyl-(1→4)-D-glucopyranosyl]urea are dissolved in a mixture of 150 ml of tetrahydrofuran and 30 ml of acetic acid, and 20 g of sodium anhydrate are added thereto. 8 g of nitrogen tetroxide gas are introduced into the mixture for 10 minutes under ice-cooling and stirring. The mixture is treated in the same manner as described in Example 43. 4.2 g of 1-(2-chloroethyl)-1-nitroso-3-n-hexyl-3-[O-α-D-glucopyranosyl-(1→4)-D-glucopyranosyl]urea (i.e., 1-(2-chloroethyl)-1-nitroso-3-n-hexyl-3-D-maltosylurea) are thereby obtained as a pale yellow powder.

M.p. 70°–72° C.(decomp.)
IR$\nu_{max}^{nujol}$(cm$^{-1}$): 3300, 1690, 1080, 1040
NMR(D$_2$O) δ: 0.70–2.10(m, —(CH$_2$)$_4$CH$_3$)
[α]$_D^{25}$+60.3°(C=1.0, methanol)

EXAMPLE 53

(1) 7.2 g of D-maltose monohydrate, 1.5 g of 2-propenylamine and 2.5 g of 2-chloroethyl isocyanate are treated in the same manner as described in Example 42-(1). 8.0 g of 1-(2-chloroethyl)-3-(2-propenyl)-3-[O-α-D-glucopyranosyl-(1→4)-D-glucopyranosyl]urea (i.e., 1-(2-chloroethyl)-3-(2-propenyl)-3-D-maltosylurea) are thereby obtained as a colorless powder.

IR$\nu_{max}^{nujol}$(cm$^{-1}$): 3350, 1645, 1540, 1070, 1030

(2) 4.8 g of 1-(2-chloroethyl)-3-(2-propenyl)-3-[O-α-D-glucopyranosyl-(1→4)-D-glucopyranosyl]urea are dissolved in a mixture of 150 ml of tetrahydrofuran and 20 ml of acetic acid, and 20 g of sodium acetate anhydrate are added thereto. 8 g of nitrogen tetroxide gas are introduced into the mixture for 10 minutes under ice-cooling and stirring. The mixture is treated in the same manner as described in Example 43. 3.2 g of 1-(2-chloroethyl)-1-nitroso-3-(2-propenyl)-3-[O-α-D-glucopyranosyl-(1→4)-D-glucopyranosyl]urea (i.e., 1-(2-chloroethyl)-1-nitroso-3-(2-propenyl)-3-D-maltosylurea) are thereby obtained as a pale yellow powder.

M.p. 67° C.(decomp.)
IR$\nu_{max}^{nujol}$(cm$^{-1}$): 3300, 1695, 1050
[α]$_D^{17}$+41.3°(C=1.4, methanol)

EXAMPLE 54

(1) 7.2 g of D-maltose monohydrate, 2.8 g of 2-methyl-2-propenylamine and 2.5 g of 2-chloroethyl isocyanate are treated in the same manner as described in Example 42-(1). 7.8 g of 1-(2-chloroethyl)-3-(2-methyl-2-propenyl)-3-[O-α-D-glucopyranosyl-(1→4)-D-glucopyranosyl]urea (i.e., 1-(2-chloroethyl)-3-(2-methyl-2-propenyl)-3-D-maltosylurea) are thereby obtained as a colorless powder.

IR$\nu_{max}^{nujol}$(cm$^{-1}$): 3350, 1640, 1535, 1070, 1030
NMR(D$_2$O) δ: 1.78(s, CH$_3$)

(2) 4.9 g of 1-(2-chloroethyl)-3-(2-methyl-2-propenyl)-3-[O-α-D-glucopyranosyl-(1→4)-D-glucopyranosyl]urea are dissolved in a mixture of 150 ml of tetrahydrofuran and 20 ml of acetic acid, and 20 g of sodium acetate anhydrate are added thereto. 8 g of nitrogen tetroxide gas are introduced into the mixture for 10 minutes under ice-cooling and stirring. The mixture is treated in the same manner as described in Example 43. 3.6 g of 1-(2-chloroethyl)-1-nitroso-3-(2-methyl-2-propenyl)-3-[O-α-D-glucopyranosyl-(1→4)-D-glucopyranosyl]urea (i.e., 1-(2-chloroethyl)-1-nitroso-3-(2-methyl-2-propenyl)-3-D-maltosylurea) are thereby obtained as a pale yellow powder.

M.p. 76°–80° C.(decomp.)
IR$\nu_{max}^{nujol}$(cm$^{-1}$): 3350, 1690, 1060, 1030
NMR(D$_2$O) δ: 1.80(s, CH$_3$)
[α]$_D^{24}$+58.1°(C=0.8, methanol)

EXAMPLE 55

(1) 7.2 g of D-maltose monohydrate, 2.1 g of 2-butenylamine and 2.5 g of 2-chloroethyl isocyanate are treated in the same manner as described in Example 42-(1). 8.2 g of 1-(2-chloroethyl)-3-(2-butenyl)-3-[O-α-D-glucopyranosyl-(1→4)-D-glucopyranosyl]urea (i.e., 1-(2-chloroethyl)-3-(2-butenyl)-3-D-maltosylurea) are thereby obtained as a colorless powder.

M.p. 71°–75° C.(decomp.)
IR$\nu_{max}^{nujol}$(cm$^{-1}$): 3350, 1640, 1530, 1070, 1030
NMR(D$_2$O) δ: 1.75(d, CH$_3$)

(2) 4.9 g of 1-(2-chloroethyl)-3-(2-butenyl)-3-[O-α-D-glucopyranosyl-(1→4)-D-glucopyranosyl]urea are dissolved in a mixture of 150 ml of tetrahydrofuran and 20 ml of acetic acid, and 20 g of sodium acetate anhydrate are added thereto. 8 g of nitrogen tetroxide gas are introduced into the mixture for 10 minutes under ice-cooling and stirring. The mixture is treated in the same manner as described in Example 43. 3.8 g of 1-(2-chloroethyl)-1-nitroso-3-(2-butenyl)-3-[O-α-D-glucopyranosyl-(1→4)-D-glucopyranosyl]urea (i.e., 1-(2-chloroethyl)-1-nitroso-3-(2-butenyl)-3-D-maltosylurea) are thereby obtained as a pale yellow powder.

M.p. 73°–76° C.(decomp.)
IR$\nu_{max}^{nujol}$(cm$^{-1}$): 3350, 1690, 1080
NMR(D$_2$O) δ: 1.65(d, CH$_3$)
[α]$_D^{24}$+43.0°(C=0.9, methanol)

EXAMPLE 56

(1) 7.2 g of D-maltose monohydrate, 2.0 g of 3-butenylamine and 2.5 g of 2-chloroethyl isocyanate are treated in the same manner as described in Example 42-(1). 8.0 g of 1-(2-chloroethyl)-3-(3-butenyl)-3-[O-α-D-glucopyranosyl-(1→4)-D-glucopyranosyl]urea (i.e., 1-(2-chloroethyl)-3-(3-butenyl)-3-D-maltosylurea) are thereby obtained as a colorless powder.

IR$\nu_{max}^{nujol}$(cm$^{-1}$): 3350, 1635, 1530, 1070, 1030
NMR(D$_2$O) δ: 2.40–2.60(m, —C$\underline{H}_2$CH=CH$_2$)

(2) 4.9 g of 1-(2-chloroethyl)-3-(3-butenyl)-3-[O-α-D-glucopyranosyl-(1→4)-D-glucopyranosyl]urea are dissolved in a mixture of 150 ml of tetrahydrofuran and 20 ml of acetic acid, and 20 g of sodium acetate anhydrate are added thereto. 8 g of nitrogen tetroxide gas are introduced into the mixture for ten minutes under ice-cooling and stirring. The mixture is treated in the same manner as described in Example 43. 3.9 g of 1-(2-chloroethyl)-1-nitroso-3-(3-butenyl)-3-[O-α-D-glucopyranosyl-(1→4)-D-glucopyranosyl]urea (i.e., 1-(2-chloroethyl)-1-nitroso-3-(3-butenyl)-3-D-maltosylurea) are thereby obtained as a pale yellow powder.

M.p. 74° C.(decomp.)
IR$\nu_{max}^{nujol}$(cm$^{-1}$): 3380, 1690, 1640, 1070, 1035
NMR(D$_2$O) δ: 2.38–2.60(m, 2H, —C$\underline{H}_2$CH=CH$_2$), 4.18(t, 2H, —N(NO)—C$\underline{H}_2$)
$[\alpha]_D^{28}$ +59.2°(C=1.0, methanol)

EXAMPLE 57

(1) 7.2 g of D-lactose monohydrate, 1.9 g of n-butylamine and 2.5 g of 2-chloroethyl isocyanate are treated in the same manner as described in Example 42-(1). 8.5 g of 1-(2-chloroethyl)-3-n-butyl-3-[O-β-D-galactopyranosyl-(1→4)-D-glucopyranosyl]urea (i.e., 1-(2-chloroethyl)-3-n-butyl-3-D-lactosylurea) are thereby obtained as a colorless powder.

IR$\nu_{max}^{nujol}$(cm$^{-1}$): 3350, 1640, 1540, 1080, 1040
NMR(D$_2$O) δ: 0.70–1.90(m, —(C$\underline{H}_2$)$_2$C$\underline{H}_3$)

(2) 5.1 g of 1-(2-chloroethyl)-3-n-butyl-3-[O-β-D-galactopyranosyl-(1→4)-D-glucopyranosyl]urea are dissolved in 20 ml of formic acid, and 2 g of sodium nitrite are added gradually thereto at 0° to 5° C. for one hour under stirring. The mixture is further stirred at the same temperature for one hour. After the reaction, the mixture is treated in the same manner as described in Example 1-(2). 0.8 g of 1-(2-chloroethyl)-1-nitroso-3-n-butyl-3-[O-β-D-galactopyranosyl-(1→4)-D-glucopyranosyl]urea (i.e., 1-(2-chloroethyl)-1-nitroso-3-n-butyl-3-D-lactosylurea) are thereby obtained as a pale yellow powder.

M.p. 90°–95° C.(decomp.)
IR$\nu_{max}^{nujol}$(cm$^{-1}$): 3400, 1690, 1080, 1050
NMR(D$_2$O) δ: 0.70–1.95(m, 7H, —(C$\underline{H}_2$)$_2$C$\underline{H}_3$), 4.20(t, 2H, —N(NO)—C$\underline{H}_2$—)
$[\alpha]_D^{20}$ +8.0°(C=0.8, methanol)

EXAMPLE 58

4.9 g of 1-(2-chloroethyl)-3-n-butyl-3-[O-β-D-galactopyranosyl-(1→4)-D-glucopyranosyl]urea are dissolved in a mixture of 150 ml of tetrahydrofuran and 20 ml of acetic acid, and 20 g of sodium acetate anhydrate are added thereto. 8 g of nitrogen tetroxide gas are introduced into the mixture for 10 minutes under ice-cooling and stirring. The mixture is treated in the same manner as described in Example 43. 3.8 g of 1-(2-chloroethyl)-1-nitroso-3-n-butyl-3-[O-β-D-galactopyranosyl-(1→4)-D-glucopyranosyl]urea (i.e., 1-(2-chloroethyl)-1-nitroso-3-n-butyl-3-D-lactosylurea) are thereby obtained as a pale yellow powder.

M.p. 90°–95° C.(decomp.)
$[\alpha]_D^{20}$ +8.0°(C=0.8, methanol)

EXAMPLE 59

(1) 7.2 g of D-lactose monohydrate, 2.5 g of isobutylamine and 2.5 g of 2-chloroethyl isocyanate are treated in the same manner as described in Example 42-(1). 8.2 g of 1-(2-chloroethyl)-3-isobutyl-3-[O-β-D-galactopyranosyl-(1→4)-D-glucopyranosyl]urea (i.e., 1-(2-chloroethyl)-3-isobutyl-3-D-lactosylurea) are thereby obtained as a colorless powder.

M.p. 99°–103° C.(decomp.)
IR$\nu_{max}^{nujol}$(cm$^{-1}$): 3350, 1630, 1525, 1070
NMR(D$_2$O) δ: 0.90(d, 6H, —CH(C$\underline{H}_3$)$_2$), 1.80–2.20(m, 1H, —C$\underline{H}$(CH$_3$)$_2$)

(2) 4.9 g of 1-(2-chloroethyl)-3-isobutyl-3-[O-β-D-galactopyranosyl-(1→4)-D-glucopyranosyl]urea are dissolved in a mixture of 150 ml of tetrahydrofuran and 20 ml of acetic acid, and 20 g of sodium acetate anhydrate are added thereto. 8 g of nitrogen tetroxide gas are introduced into the mixture for 10 minutes under ice-cooling and stirring. The mixture is treated in the same manner as described in Example 43. 4.0 g of 1-(2-chloroethyl)-1-nitroso-3-isobutyl-3-[O-β-D-galactopyranosyl-(1→4)-D-glucopyranosyl]urea (i.e., 1-(2-chloroethyl)-1-nitroso-3-isobutyl-3-D-lactosylurea) are thereby obtained as a pale yellow powder.

M.p. 87°–92° C.(decomp.)
IR$\nu_{max}^{nujol}$(cm$^{-1}$): 3400, 1690, 1070
NMR(D$_2$O) δ: 0.93(d, 6H, —CH(C$\underline{H}_3$)$_2$), 1.85–2.20(m, 1H, —C$\underline{H}$(CH$_3$)$_2$)
$[\alpha]_D^{20}$ −4.0°(C=1.0, methanol)

EXAMPLE 60

(1) 1.5 g of N-methyl-ethanolamine are dissolved in 30 ml of tetrahydrofuran, and 2.1 g of 2-chloroethyl isocyanate is added dropwise thereto at 0° to 5° C. The solution is stirred at room temperature for 1.5 hours. Then, the reaction solution is condensed under reduced pressure, 3.5 g of 1-(2-chloroethyl)-3-methyl-3-(2-hydroxyethyl)urea are obtained as a colorless oil.

IR$\nu_{max}^{liq}$(cm$^{-1}$): 3320, 1620, 1530
Mass(m/e): 182, 180(M+)

(2) 0.9 g of 1-(2-chloroethyl)-3-methyl-3-(2-hydroxyethyl)urea is dissolved in 10 ml of acetic acid, and 0.9 g of sodium nitrite is added thereto under stirring. The mixture is stirred at room temperature for one hour. Then, 0.5 g of sodium nitrite is again added to the mixture, and said mixture is further stirred at the same temperature for 4 hours. After the reaction, the mixture is freeze-dried, and the residue obtained is purified by silica gel chromatography (Solvent: chloroform-methanol=10:1). 0.7 g of 1-(2-chloroethyl)-1-nitroso-3-methyl-3-(2-hydroxyethyl)urea is thereby obtained as a pale yellow oil.

IR$\nu_{max}^{liq}$(cm$^{-1}$): 3400, 1700
NMR(CDCl$_3$) δ: 2.85(s, 1H, OH), 3.23(s, 3H, CH$_3$), 3.60–4.25(m, 8H, C$\underline{H}_2$C$\underline{H}_2$OH, C$\underline{H}_2$C$\underline{H}_2$Cl)
Mass(m/e): 211, 209(M+)

EXAMPLE 61

(1) 2.1 g of diethanolamine are dissolved in 30 ml of tetrahydrofuran, and 2.1 g of 2-chloroethyl isocyanate is added dropwise thereto at 0° to 5° C. The solution is stirred at room temperature for 2 hours. Then, the reaction solution is condensed under reduced pressure. 4.2 g of 1-(2-chloroethyl)-3,3-bis(2-hydroxyethyl)urea are obtained as a colorless oil.

IR$\nu_{max}^{liq}$(cm$^{-1}$): 3330, 1620, 1540

(2) 4.0 g of 1-(2-chloroethyl)-3,3-bis(2-hydroxyethyl)urea are dissolved in 30 ml of acetic acid, and 2.5 g of sodium nitrite are added thereto under stirring. The mixture is stirred at room temperature for 4 hours. After the reaction, the mixture is treated in the same manner as described in Example 60-(2) (Solvent used for chromatography: chloroform-methanol (10:1)). 3.0 g of 1-(2-chloroethyl)-1-nitroso-3,3-bis(2-hydroxyethyl)urea are thereby obtained as a yellow oil.

IR$\nu_{max}^{liq}$(cm$^{-1}$): 3370, 1690

NMR(CDCl$_3$) δ: 3.40–4.00(m, 10H, C$\underline{H}_2$C$\underline{H}_2$OH, CH$_2$C$\underline{H}_2$Cl), 4.10(t, 2H, —N(NO)C$\underline{H}_2$—), 4.50(broad s, 2H, O$\underline{H}$)

EXAMPLE 62

(1) A mixture of 3.3 g of 3-chloro-1,2-dihydroxy-n-propane and 20 ml of 30% methylamine-methanol solution is allowed to stand at room temperature for 3 days. The reaction mixture is condensed to dryness under reduced pressure, whereby 4.2 g of N-methyl-2,3-dihydroxy-n-propylamine hydrochloride are obtained as a crude product. 4.2 g of said crude product and 3 g of triethylamine are dissolved in 30 ml of methanol. To the solution, 3.2 g of 2-chloroethyl isocyanate are added dropwise to the solution at 0° to 5° C. The solution is stirred at room temperature for 2 hours. Then, the reaction solution is condensed under reduced pressure and the residue thus obtained is purified by silica gel chromatography (Solvent: chloroform-ethyl acetate-methanol(3:1:1)). 3.5 g of 1-(2-chloroethyl)-3-methyl-3-(2,3-dihydroxy-n-propyl)urea are obtained as a colorless oil.

IR$\nu_{max}^{liq}$(cm$^{-1}$): 3350, 1630, 1540

Mass(m/e): 210(M+ weak), 143(B+)

(2) 2.1 g of 1-(2-chloroethyl)-3-methyl-3-(2,3-dihydroxy-n-propyl)urea are dissolved in 10 ml of acetic acid, and 1.4 g of sodium nitrite are added thereto under stirring. The mixture is stirred at room temperature for 2 hours. Then, 2 ml of concentrated hydrochloric acid and one g of sodium nitrite are added to the mixture, and said mixture is further stirred at the same temperature for 2 hours. After the reaction, the mixture is treated in the same manner as described in Example 60-(2) (Solvent used for chromatography: chloroform-ethyl acetate-methanol(3:1:1)). 1.5 g of 1-(2-chloroethyl)-1-nitroso-3-methyl-3-(2,3-dihydroxy-n-propyl)urea are thereby obtained as a pale yellow oil.

IR$\nu_{max}^{liq}$(cm$^{-1}$): 3400, 1690

NMR(D$_2$O) δ: 3.20(s, 3H, CH$_3$), 3.40–3.90(m, 7H, C$\underline{H}_2$C$\underline{H}$(OH)— C$\underline{H}_2$OH, CH$_2$CH$_2$Cl), 4.20(t, 2H, —N(NO)—C$\underline{H}_2$—), 4.78(broad s, 2H, O$\underline{H}$)

EXAMPLE 63

(1) 6.1 g of 1-n-butylamino-1-deoxy-2,4-O-ethylidene-D-erythritol(prepared from 2,4-O-ethylidene-D-erythrose according to the method of Ziderman (I. Ziderman and E. Dimant, J. Org. Chem., 31, 223 (1966))) are dissolved in 20 ml of 10% aqueous hydrochloric acid and the solution is heated at 80° C. for one hour. The reaction mixture is condensed to dryness under reduced pressure, whereby 6.4 g of 1-n-butylamino-1-deoxy-D-erythritol hydrochloride are obtained as a crude product. 6.4 g of said crude product and 3 g of triethylamine are dissolved in 40 ml of methanol. 3.2 g of 2-chloroethyl isocyanate are added dropwise to the solution at 0° to 5° C. The the reaction mixture is treated in the same manner as described in Example 62-(1). 5.0 g of 1-(2-chloroethyl)-3-n-butyl-3-(1-deoxy-D-erythritolyl)urea are obtained as a colorless oil.

IR$\nu_{max}^{liq}$(cm$^{-1}$): 3320, 1620, 1540, 1260, 1070

(2) 3.1 g of 1-(2-chloroethyl)-3-n-butyl-3-(1-deoxy-D-erythritolyl)urea are dissolved in 10 ml of formic acid, and 1.4 g of sodium nitrite are added thereto. The mixture is stirred at 0° to 5° C. for 3 hours. After the reaction, the mixture is treated in the same manner as described in Example 62-(2). 2.0 g of 1-(2-chloroethyl)-1-nitroso-3-n-butyl-3-(1-deoxy-D-erythritolyl)urea are thereby obtained as a yellow oil.

IR$\nu_{max}^{liq}$(cm$^{-1}$): 3400, 1680, 1080

NMR(CDCl$_3$) δ: 0.80–1.80(m, 7H, C$\underline{H}_2$C$\underline{H}_2$CH$_3$), $[\alpha]_D^{26}$ −23.5°(C=0.9, methanol)

EXAMPLE 64

(1) A mixture of 3.3 g of 3-chloro-1,2-dihydroxy-n-propane and 8 g of n-propylamine is allowed to stand at room temperature for 5 days. The reaction mixture is condensed to dryness under reduced pressure, whereby 5.0 g of N-n-propyl-2,3-dihydroxy-n-propylamine hydrochloride are obtained as a crude product. 5.0 g of said crude product and 3 g of triethylamine are dissolved in 40 ml of methanol. 3.2 g of 2-chloroethyl isocyanate are added to the solution at 0° to 5° C. Then, the reaction mixture is treated in the same manner as described in Example 62-(1). 3.0 g of 1-(2-chloroethyl)-3-n-propyl-3-(2,3-dihydroxy-n-propyl)urea are obtained as a colorless oil.

IR$\nu_{max}^{liq}$(cm$^{-1}$): 3300, 1620, 1530, 1260, 1050

Mass(m/e): 238(M+ very weak), 171(B+)

(2) 3 g 1-(2-chloroethyl)-3-n-propyl-3-(2,3-dihydroxy-n-propyl)urea are dissolved in 10 ml of acetic acid, and 1.5 g of sodium nitrite are added thereto under stirring. The mixture is stirred at the same temperature for 4 hours. After the reaction, the mixture is treated in the same manner as described in Example 62-(2). 1.7 g of 1-(2-chloroethyl)-1-nitroso-3-n-propyl-3-(2,3-dihydroxy-n-propyl)urea are thereby obtained as a yellow oil.

IR$\nu_{max}^{liq}$(cm$^{-1}$): 3400, 1685, 1080

NMR(CDCl$_3$) δ: 0.90(t, 3H, —CH$_2$C$\underline{H}_3$), 1.30–2.00(m, 2H, —CH$_2$C$\underline{H}_2$CH$_3$),

EXAMPLE 65

(1) A solution of 1.6 g of 2-chloroethyl isocyanate in 5 ml of tetrahydrofuran is added under ice-cooling to 50 ml of a methanol solution containing 2.9 g of N-methylglucamine, and the mixture is stirred at room temperature for one hour. After the reaction, the mixture is condensed under reduced pressure. The residue obtained is recrystallized from a mixture of ethanol and ethyl acetate. 3.5 g of 1-(2-chloroethyl)-3-methyl-3-(1-deoxy-D-glucitolyl)urea are thereby obtained as colorless crystals.

M.p. 88°–90° C.

IR$\nu_{max}^{nujol}$(cm$^{-1}$): 3350, 3270, 1630, 1540

(2) 1.9 g of 1-(2-chloroethyl)-3-methyl-3-(1-deoxy-D-glucitolyl)urea are dissolved in 10 ml of formic acid, and 0.9 g of sodium nitrite is added gradually thereto at 0° to 5° C. for one hour under stirring. The mixture is further stirred at the same temperature for 30 minutes. After the reaction, the mixture is freeze-dried. The residue thus obtained is purified by silica gel chromatography (Solvent: chloroform-ethyl acetate-methanol(2:1:1)). 0.7 g of 1-(2-chloroethyl)-1-nitroso-3- methyl-3-(1-deoxy-D-glucitolyl)urea is thereby obtained as pale yellow caramel.

IR$\nu_{max}^{nujol}$(cm$^{-1}$): 3330, 1690, 1080

NMR(D$_2$O) δ: 3.23(s, 3H, C$\underline{H}_3$), 4.20(t, 2H, —N(-NO)—C$\underline{H}_2$—)

$[\alpha]_D^{26}$ −14.7°(C=1.1, methanol)

EXAMPLE 66

(1) 2.4 g of N-n-butylglucamine prepared by the hydrogenolysis of 1-n-butylamino-1-deoxy-D-glucose (see; F. Kagan et al., J. Am. Chem. Soc., 79, 3541 (1957)) and 1.1 g of 2-chloroethyl isocyanate are treated in the same manner as described in Example 65-(1). 3.5 g of 1-(2-chloroethyl)-3-n-butyl-3-(1-deoxy-D-glucitolyl)urea are thereby obtained as colorless caramel.

IR$\nu_{max}^{liq}$(cm$^{-1}$): 3350, 1620, 1540, 1080

(2) 4 g of 1-(2-chloroethyl)-3-n-butyl-3-(1-deoxy-D-glucitolyl)urea are dissolved in 15 ml of formic acid, and 2.5 g of sodium nitrite are added gradually thereto for one hour under ice-cooling. The mixture is stirred for 30 minutes. After the reaction, the mixture is treated in the same manner as described in Example 65-(2) (Solvent used for the chromatography: chloroform-methanol(5:1)). 1.8 g of 1-(2-chloroethyl)-1-nitroso-3-n-butyl-3-(1-deoxy-D-glucitolyl)urea are thereby obtained as a pale yellow powder.

M.p. 65°–67° C.(decomp.)

IR$\nu_{max}^{nujol}$(cm$^{-1}$): 3300, 1700, 1130, 1090

NMR(D$_2$O) δ: 0.70–0.90(m, 7H, —C$\underline{H}_2$C$\underline{H}_2$C$\underline{H}_3$), 4.15(t, 2H, —N(NO)—CH$_2$)

$[\alpha]_D^{26}$ −17.8°(C=1.5, methanol)

What we claim is:

1. A compound of the formula:

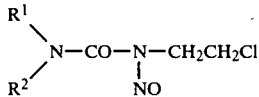

wherein R$^1$ is a group selected from the class consisting of alkyl of one to six carbon atoms, hydroxyalkyl of one to six carbon atoms, alkenyl of three to five carbon atoms and alkynyl of three to five carbon atoms, R$^2$ is a group selected from the class consisting of D-glucopyranosyl, D-galactopyranosyl, D-mannopyranosyl, D-xylopyranosyl, L-arabinopyranosyl, O-α-D-glucopyranosyl-(1→4)-D-glucopyranosyl and a group of the formula: —CH$_2$(CHOH)$_n$CH$_2$OH, and n is zero or an integer of one to four.

2. The compound of claim 1, in which R$^1$ is a group selected from the class consisting of alkyl of one to five carbon atoms, alkenyl or alkynyl of three to four carbon atoms and 2-hydroxyethyl.

3. The compound of claim 1, in which R$^1$ is a group selected from the class consisting of alkyl of one to five carbon atoms, alkenyl of three to four carbon atoms, alkynyl of three carbon atoms and 2-hydroxyethyl.

4. The compound of claim 2 or 3, in which R$^2$ is a group selected from the class consisting of D-galactopyranosyl, D-glucopyranosyl, L-rhamnopyranosyl, D-ribofuranosyl, D-mannopyranosyl, D-xylopyranosyl, L-arabinopyranosyl, O-α-D-glucopyranosyl-(1→4)-D-glucopyranosyl, O-β-D-galactopyranosyl-(1→4)-D-glucopyranosyl and a group of the formula: —CH$_2$(CHOH)$_n$CH$_2$OH, wherein n is zero or an integer of one to four.

5. The compound of claim 3, in which R$^1$ is a group selected from the class consisting of alkyl of one to five carbon atoms and alkenyl of three to four carbon atoms, and R$^2$ is a group selected from the class consisting of D-glucopyranosyl, D-galactopyranosyl, D-mannopyranosyl, D-xylopyranosyl, L-arabinopyranosyl, O-α-D-glucopyranosyl-(1→4)-D-glucopyranosyl and a group of the formula: —CH$_2$(CHOH)$_m$CH$_2$OH, wherein m is an integer of one, two or four.

6. The compound of claim 5, in which R$^1$ is a group selected from the class consisting of methyl, ethyl, n-propyl, isopropyl, n-butyl, isobutyl, n-pentyl, isopentyl, neopentyl, 2-n-propenyl, 2-methyl-2-n-propenyl, 2-n-butenyl and 3-n-butenyl.

7. The compound of claim 5, in which R$^1$ is a group selected from the class consisting of methyl, ethyl, n-propyl, isopropyl, n-butyl, isobutyl, n-pentyl, isopentyl, neopentyl, 2-n-propenyl, 2-methyl-2-n-propenyl and 2-n-butenyl.

8. The compound of claim 5, in which R$^1$ is a group selected from the class consisting of methyl, ethyl, n-propyl, isopropyl, n-butyl, isobutyl, n-pentyl, neopentyl, 2-n-propenyl, 2-methyl-2-n-propenyl and 2-n-butenyl.

9. The compound of claim 5, in which R$^1$ is a group selected from the class consisting of ethyl, n-propyl, isopropyl, n-butyl, isobutyl, n-pentyl, neopentyl, 2-n-propenyl, 2-methyl-2-n-propenyl and 2-n-butenyl.

10. The compound of claim 3, in which R$^1$ is a group selected from the class consisting of alkyl of two to five carbon atoms, alkenyl of three to four carbon atoms and 2-hydroxyethyl, and R$^2$ is a group selected from the class consisting of D-glucopyranosyl, D-galactopyranosyl, D-mannopyranosyl, D-xylopyranosyl, L-arabinopyranosyl, O-α-D-glucopyranosyl-(1→4)-D-glucopyranosyl and a group of the formula: —CH$_2$(CHOH)$_m$CH$_2$OH, wherein m is an integer of one, two or four.

11. The compound of claim 10, in which R$^1$ is alkyl of two to five carbon atoms or alkenyl of three to four carbon atoms.

12. The compound of claims 2, 3, 5, 6, 10 or 11, in which R$^2$ is a group selected from the class consisting of D-glucopyranosyl, D-galactopyranosyl, L-arabinopyranosyl, O-α-D-glucopyranosyl-(1→4)-D-glucopyranosyl, 2,3-dihydroxy-n-propyl and 2,3,4-trihydroxy-n-butyl.

13. The compound of claim 12, in which R$^1$ is a group selected from the class consisting of methyl, ethyl, n-propyl, isopropyl, n-butyl, isobutyl, n-pentyl, isopentyl, neopentyl, 2-n-propenyl, 2-n-propynyl, 2-methyl-2-n-propenyl and 2-n-butenyl.

14. The compound of claim 12, in which R$^1$ is a group selected from the class consisting of methyl, ethyl, n-propyl, isopropyl, n-butyl, isobutyl, n-pentyl, neopentyl, 2-propenyl, 2-methyl-2-n-propenyl and 2-n-butenyl.

15. The compound of claim 12, in which R$^1$ is a group selected from the class consisting of ethyl, n-propyl, isopropyl, n-butyl, isobutyl, n-pentyl, neopentyl, 2-n-propenyl, 2-methyl-2-n-propenyl and 2-n-butenyl.

16. The compound of claim 9, in which R$^1$ is a group selected from the class consisting of n-butyl, isobutyl and 2-methyl-2-n-propenyl, and R$^2$ is a group selected from the class consisting of D-galactopyranosyl, L-arabinopyranosyl and O-α-D-glucopyranosyl-(1→4)-D-glucopyranosyl.

17. The compound of claim 15, in which R$^1$ is a group selected from the class consisting of n-butyl, isobutyl and 2-methyl-2-n-propenyl, and R² is a group selected from the class consisting of D-galactopyranosyl, L-arabinopyranosyl and O-α-D-glucopyranosyl-(1→4)-D-glucopyranosyl.

18. The compound of claim 15, in which R¹ is a group selected from the class consisting of ethyl, n-propyl, isopropyl, n-butyl and isobutyl, and R² is D-glucopyranosyl.

19. The compound of claim 15, in which R¹ is a group selected from the class consisting of isopropyl, n-butyl, isobutyl, neopentyl and 2-n-propenyl, and R² is D-galactopyranosyl.

20. The compound of claim 15, in which R¹ is a group selected from the class consisting of n-propyl, isopropyl, n-butyl, isobutyl, n-pentyl, 2-n-propenyl, 2-methyl-2-n-propenyl and 2-n-butenyl, and R² is O-α-D-glucopyranosyl-(1→4)-D-glucopyranosyl.

21. The compound of claim 12, in which R¹ is a group selected from the class consisting of n-propyl, isopropyl, n-butyl, isobutyl, n-pentyl, 2-n-propenyl, 2-methyl-2-n-propenyl, 2-n-butenyl and 3-n-butenyl, and R² is O-α-D-glucopyranosyl-(1→4)-D-glucopyranosyl.

22. The compound of claim 15, in which R¹ is a group selected from the class consisting of n-propyl, isopropyl, isobutyl and 2-n-propenyl, and R² is L-arabinopyranosyl.

23. The compound of claim 15, in which R¹ is n-butyl, and R² is 2,3-dihydroxy-n-propyl or 2,3,4-trihydroxy-n-butyl.

24. The compound of claim 17 which is 1-(2-chloroethyl)-1-nitroso-3-n-butyl-3-[O-α-D-glucopyranosyl-(1→4)-D-glucopyranosyl]urea.

25. The compound of claim 17 which is 1-(2-chloroethyl)-1-nitroso-3-isobutyl-3-[O-α-D-glucopyranosyl-(1→4)-D-glucopyranosyl]urea.

26. The compound of claim 17 which is 1-(2-chloroethyl)-1-nitroso-3-(2-methyl-2-n-propenyl)-3-[O-α-D-glucopyranosyl-(1→4)-D-glucopyranosyl]urea.

27. The compound of claim 17 which is 1-(2-chloroethyl)-1-nitroso-3-n-butyl-3-D-galactopyranosylurea.

28. The compound of claim 17 which is 1-(2-chloroethyl)-1-nitroso-3-isobutyl-3-D-galactopyranosylurea.

29. The compound of claim 17 which is 1-(2-chloroethyl)-1-nitroso-3-isobutyl-3-L-arabinopyranosylurea.

30. The compound of claim 18 which is 1-(2-chloroethyl)-1-nitroso-3-ethyl-3-D-glucopyranosylurea.

31. The compound of claim 18 which is 1-(2-chloroethyl)-1-nitroso-3-isopropyl-3-D-glucopyranosylurea.

32. The compound of claim 18 which is 1-(2-chloroethyl)-1-nitroso-3-n-butyl-3-glucopyranosylurea.

33. The compound of claim 18 which is 1-(2-chloroethyl)-1-nitroso-3-isobutyl-3-D-glucopyranosylurea.

34. The compound of claim 19 which is 1-(2-chloroethyl)-1-nitroso-3-isopropyl-3-D-galactopyranosylurea.

35. The compound of claim 19 which is 1-(2-chloroethyl)-1-nitroso-3-neopentyl-3-D-galactopyranosylurea.

36. The compound of claim 19 which is 1-(2-chloroethyl)-1-nitroso-3-(2-n-propenyl)-3-D-galactopyranosylurea.

37. The compound of claim 20 which is 1-(2-chloroethyl)-1-nitroso-3-n-propyl-3-[O-α-D-glucopyranosyl-(1→4)-D-glucopyranosyl]urea.

38. The compound of claim 20 which is 1-(2-chloroethyl)-1-nitroso-3-n-pentyl-3-[O-α-D-glucopyranosyl-(1→4)-D-glucopyranosyl]urea.

39. The compound of claim 20 which is 1-(2-chloroethyl)-1-nitroso-3-(2-propenyl)-3-(O-α-D-glucopyranosyl-(1→4)-D-glucopyranosyl]urea.

40. The compound of claim 20 which is 1-(2-chloroethyl)-1-nitroso-3-(2-n-butenyl)-3-[O-α-D-glucopyranosyl-(1→4)-D-glucopyranosyl]urea.

41. The compound of claim 22 which is 1-(2-chloroethyl)-1-nitroso-3-n-propyl-3-L-arabinopyranosylurea.

42. The compound of claim 22 which is 1-(2-chloroethyl)-1-nitroso-3-isopropyl-3-L-arabinopyranosylurea.

43. The compound of claim 22 which is 1-(2-chloroethyl)-1-nitroso-3-(2-n-propenyl)-3-L-arabinopyranosylurea.

44. A therapeutic composition which comprises a therapeutically effective amount of the compound claimed in claim 1 and a pharmaceutically acceptable carrier therefor.

45. The composition of claim 44 suitable for administration to a warm blooded animal providing for a dosage of said compound between 0.1 and 30 mg/kg of body weight per day.

46. The composition of claim 45 wherein said dosage is between 0.2 and 10 mg/kg of body weight per day.

47. A method of treating transplanted tumors or leukemia in a warm blooded animal comprising administering to said animal a therapeutically effective amount of the compound of claim 1.

* * * * *